US012667286B2

(12) United States Patent
Hoss et al.

(10) Patent No.: US 12,667,286 B2
(45) Date of Patent: Jun. 30, 2026

(54) ANALYTE SENSORS FEATURING WORKING ELECTRODE ASPERITY PLANING FOR DECREASING INTERFERENT SIGNAL

(71) Applicant: ABBOTT DIABETES CARE INC., Alameda, CA (US)

(72) Inventors: Udo Hoss, San Ramon, CA (US); Mark Stephen Yahnke, Alameda, CA (US); Tahir S. Khan, Fremont, CA (US); Jean-Pierre Babka, Alameda, CA (US); Owen Daniel Reynolds, Cricklade (GB)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/347,829

(22) Filed: Jun. 15, 2021

(65) Prior Publication Data

US 2021/0386339 A1 Dec. 16, 2021

Related U.S. Application Data

(60) Provisional application No. 63/039,768, filed on Jun. 16, 2020.

(51) Int. Cl.
*B23K 26/361* (2014.01)
*A61B 5/145* (2006.01)
(Continued)

(52) U.S. Cl.
CPC ...... *A61B 5/14865* (2013.01); *A61B 5/14532* (2013.01); *B23K 26/0869* (2013.01);
(Continued)

(58) Field of Classification Search
CPC ............ A61B 5/14865; A61B 5/14532; A61B 2562/125; B23K 26/361; B23K 26/0869; B23K 26/38
See application file for complete search history.

(56) References Cited

U.S. PATENT DOCUMENTS 5,089,112 A 2/1992 Skotheim et al.
5,165,407 A 11/1992 Wilson et al.
(Continued)

FOREIGN PATENT DOCUMENTS

DK PA 2004 01265 8/2004
EP 0 838 230 A2 4/1998
(Continued)

OTHER PUBLICATIONS

Chen et al., "Defining the Period of Recovery of the Glucose Concentration after Its Local Perturbation by the Implantation of a Miniature Sensor," Clin Chem Lab Med 40(8):786-789 (2002).
(Continued)

*Primary Examiner* — Alex M Valvis
*Assistant Examiner* — Grace L Rozanski
(74) *Attorney, Agent, or Firm* — Baker Botts L.L.P.

(57) ABSTRACT

Analyte sensors are being increasingly employed for monitoring various analytes in vivo. Analyte sensors may feature enhancements to address signals obtained from interferent species. Some analyte sensors may comprise an analyte sensor comprising a working electrode comprising an active area disposed thereon and electrode asperities laser planed therefrom, the active area comprising an analyte-responsive enzyme. Methods include laser singulating a working electrode, the working electrode comprising an active area disposed thereupon and electrode asperities, the active area comprising an analyte-responsive enzyme, and laser planing at least a portion of the electrode asperities.

24 Claims, 11 Drawing Sheets

(51) Int. Cl.
*A61B 5/1486* (2006.01)
*B23K 26/08* (2014.01)
*B23K 26/38* (2014.01)

(52) U.S. Cl.
CPC ............ *B23K 26/361* (2015.10); *B23K 26/38* (2013.01); *A61B 2562/125* (2013.01)

(56) References Cited

U.S. PATENT DOCUMENTS

| | | | |
|---|---|---|---|
| 5,322,063 A | 6/1994 | Allen et al. | |
| 5,390,671 A | 2/1995 | Lord et al. | |
| 5,569,186 A | 10/1996 | Lord et al. | |
| 5,584,813 A | 12/1996 | Livingston et al. | |
| 5,849,174 A | 12/1998 | Sanghera et al. | |
| 6,103,033 A | 8/2000 | Say et al. | |
| 6,134,461 A | 10/2000 | Say et al. | |
| 6,237,394 B1 | 5/2001 | Harris et al. | |
| 6,424,847 B1 | 7/2002 | Mastrototaro et al. | |
| 6,565,509 B1 | 5/2003 | Say et al. | |
| 6,605,200 B1 | 8/2003 | Mao et al. | |
| 6,605,201 B1 | 8/2003 | Mao et al. | |
| 6,673,022 B1 | 1/2004 | Bobo et al. | |
| 6,736,957 B1 | 5/2004 | Forrow et al. | |
| 6,809,653 B1 | 10/2004 | Mann et al. | |
| 6,850,859 B1 | 2/2005 | Schuh | |
| 6,931,327 B2 | 8/2005 | Goode, Jr. et al. | |
| 6,990,366 B2 | 1/2006 | Say et al. | |
| 7,299,082 B2 | 11/2007 | Feldman et al. | |
| 7,323,142 B2 | 1/2008 | Pendo et al. | |
| 7,501,053 B2 | 3/2009 | Karinka et al. | |
| 7,725,148 B2 | 5/2010 | Shah et al. | |
| 7,754,093 B2 | 7/2010 | Forrow et al. | |
| 8,268,143 B2 | 9/2012 | Liu et al. | |
| 8,280,474 B2 | 10/2012 | Liu et al. | |
| 8,444,834 B2* | 5/2013 | Liu | C12Q 1/002 548/101 |
| 8,983,568 B2 | 3/2015 | Bommakanti et al. | |
| 9,241,631 B2 | 1/2016 | Valdes et al. | |
| 9,504,471 B2 | 11/2016 | Vaitekunas et al. | |
| 9,788,766 B2 | 10/2017 | Simpson et al. | |
| 9,808,574 B2 | 11/2017 | Yodfat et al. | |
| 10,624,568 B2* | 4/2020 | Böhm | G01N 33/49 |
| 10,820,842 B2 | 11/2020 | Harper | |
| 10,827,954 B2 | 11/2020 | Hoss et al. | |
| 10,874,338 B2 | 12/2020 | Stafford | |
| 10,881,341 B1 | 1/2021 | Curry et al. | |
| 10,945,647 B2 | 3/2021 | Mazza et al. | |
| 10,945,649 B2 | 3/2021 | Lee et al. | |
| 10,952,653 B2 | 3/2021 | Harper | |
| 10,959,654 B2 | 3/2021 | Curry et al. | |
| 10,966,644 B2 | 4/2021 | Stafford | |
| 10,973,443 B2 | 4/2021 | Funderburk et al. | |
| 10,980,461 B2 | 4/2021 | Simpson et al. | |
| 11,000,213 B2 | 5/2021 | Kamath et al. | |
| 11,000,216 B2 | 5/2021 | Curry et al. | |
| 11,013,440 B2 | 5/2021 | Lee et al. | |
| 11,064,917 B2 | 7/2021 | Simpson et al. | |
| 11,141,084 B2 | 10/2021 | Funderburk et al. | |
| 2002/0161288 A1 | 10/2002 | Shin et al. | |
| 2002/0169369 A1 | 11/2002 | Ward et al. | |
| 2003/0042137 A1 | 3/2003 | Mao et al. | |
| 2003/0097082 A1 | 5/2003 | Purdy et al. | |
| 2003/0114836 A1 | 6/2003 | Estes et al. | |
| 2003/0225361 A1 | 12/2003 | Sabra | |
| 2004/0061232 A1 | 4/2004 | Shah et al. | |
| 2004/0087876 A1 | 5/2004 | Eskuri | |
| 2005/0027181 A1 | 2/2005 | Goode, Jr. et al. | |
| 2005/0038332 A1 | 2/2005 | Saidara et al. | |
| 2005/0215871 A1 | 9/2005 | Feldman et al. | |
| 2005/0245799 A1 | 11/2005 | Brauker et al. | |
| 2006/0020187 A1 | 1/2006 | Brister et al. | |
| 2006/0094944 A1 | 5/2006 | Chuang | |
| 2006/0142651 A1 | 6/2006 | Brister et al. | |
| 2006/0200982 A1 | 9/2006 | Bhullar et al. | |
| 2006/0257996 A1 | 11/2006 | Simpson et al. | |
| 2006/0258959 A1 | 11/2006 | Sode | |
| 2008/0161666 A1 | 7/2008 | Feldman et al. | |
| 2008/0172205 A1 | 7/2008 | Breton et al. | |
| 2008/0194990 A1 | 8/2008 | Heller et al. | |
| 2008/0319414 A1 | 12/2008 | Yodfat et al. | |
| 2009/0076360 A1 | 3/2009 | Brister et al. | |
| 2009/0099521 A1 | 4/2009 | Gravesen et al. | |
| 2009/0102678 A1 | 4/2009 | Mazza et al. | |
| 2009/0178459 A1 | 7/2009 | Li et al. | |
| 2010/0145377 A1 | 6/2010 | Lai et al. | |
| 2010/0193484 A1* | 8/2010 | Chen | B23K 26/362 219/121.75 |
| 2010/0230285 A1 | 9/2010 | Hoss et al. | |
| 2010/0286496 A1 | 11/2010 | Simpson et al. | |
| 2011/0213225 A1 | 9/2011 | Bernstein et al. | |
| 2012/0150005 A1 | 6/2012 | Hoss et al. | |
| 2013/0118920 A1 | 5/2013 | Craggs et al. | |
| 2013/0345534 A1 | 12/2013 | Hoss et al. | |
| 2015/0005601 A1 | 1/2015 | Hoss et al. | |
| 2015/0094554 A1 | 4/2015 | Heller et al. | |
| 2015/0298124 A1* | 10/2015 | Fischer | B01L 3/50273 204/604 |
| 2015/0351690 A1 | 12/2015 | Toth et al. | |
| 2016/0235347 A1 | 8/2016 | Baig et al. | |
| 2017/0107555 A1 | 4/2017 | Katsuki et al. | |
| 2017/0112531 A1 | 4/2017 | Schoonmaker et al. | |
| 2017/0188908 A1* | 7/2017 | Hoss | A61B 5/14532 |
| 2017/0265795 A1 | 9/2017 | Boock et al. | |
| 2017/0273610 A1 | 9/2017 | Suri et al. | |
| 2017/0363564 A1 | 12/2017 | Hoss et al. | |
| 2018/0199873 A1* | 7/2018 | Wang | C12Q 1/006 |
| 2018/0328877 A1 | 11/2018 | Vaddiraju et al. | |
| 2019/0125230 A1 | 5/2019 | Feldman | |
| 2019/0175083 A1 | 6/2019 | Cohen et al. | |
| 2019/0216374 A1 | 7/2019 | Hoss et al. | |
| 2019/0261907 A1 | 8/2019 | Brister et al. | |
| 2019/0298232 A1 | 10/2019 | Ko et al. | |
| 2019/0310222 A1 | 10/2019 | Boock | |
| 2019/0320947 A1 | 10/2019 | Chen et al. | |
| 2019/0326501 A1* | 10/2019 | Gilbert | C04B 35/45 |
| 2020/0022670 A1* | 1/2020 | Eibl | A61B 8/4488 |
| 2020/0060592 A1 | 2/2020 | Feldman et al. | |
| 2020/0146595 A1 | 5/2020 | Simpson et al. | |
| 2020/0178862 A1 | 6/2020 | Brister | |
| 2020/0178864 A1 | 6/2020 | Cui et al. | |
| 2020/0188660 A1* | 6/2020 | Franke | A61N 1/36071 |
| 2020/0237275 A1 | 7/2020 | Feldman et al. | |
| 2020/0237277 A1 | 7/2020 | Ouyang et al. | |
| 2020/0241015 A1 | 7/2020 | Ouyang et al. | |

FOREIGN PATENT DOCUMENTS

| | | |
|---|---|---|
| GB | 2 067 764 A | 7/1981 |
| WO | WO 98/56293 A1 | 12/1998 |
| WO | WO 99/56613 A1 | 11/1999 |
| WO | WO 03/056319 A2 | 7/2003 |
| WO | WO 2004/088275 A2 | 10/2004 |
| WO | WO 2006/018447 A2 | 2/2006 |
| WO | WO 2006/042811 A2 | 4/2006 |
| WO | WO 2010/091005 A1 | 8/2010 |

OTHER PUBLICATIONS

DCU Conferences, Nov. 2003, 8 pgs.
Declaration of John Mastrototaro, PH.D., 205 pgs. (Sep. 29, 2022).
Dexcom 10K, 59 pgs. (2005).
DexCom CGM Resource Center References Bibliography, 14 pgs. (Jun. 12, 2011).
Dexcom SEC Form, S-1-2005, 309 pgs. (Feb. 1, 2005).
Diabetes Abstract Book, 53(2):1-12 (Jun. 2004).
FDA Notice-Determination of Regulatory, Federal Registry 86(211):60827-60829 (Nov. 4, 2021) 3 pgs.
FDA Premarket Approval (PMA) for Freestyle Navigator Continuous Glucose Monitor, Jan. 23, 2022, 6 pgs.
Feldman et al., "A Continuous Glucose Sensor Based on Wired Enzyme Technology-Results from a 3-Day Trial in Patients with Type 1 Diabetes," Diabetes Technology & Thgerapeutics 5(5):769-779 (2003).

(56) References Cited

OTHER PUBLICATIONS

Freestyle Navigator User Guide, (Mar. 6, 2000) 38 pgs.
Heinemann et al., "Benefits and Limitations of MARD as a Performance Parameter for Continuous Glucose Monitoring in the Interstitial Space," Journal of Diabetes Science and Technology 14(1):135-150 (2020).
Heller et al., "Electrochemical Glucose Sensors and Their Applications in Diabetes Management," Chem. Rev. 108:2482-2505 (2008).
Heller et al., "Electrochemistry in Diabetes Management," Accounts of Chemical Research 43(7):963-973 (2010).
Heller, "Integrated Medical Feedback Systems for Drug Delivery," AIChE Journal 51(4):1054-1066 (2005).
International Search Report and Written Opinion mailed Sep. 24, 2021 in International Application No. PCT/US2021/037307.
International Search Report and Written Opinion mailed Sep. 24, 2021 in International Application No. PCT/US2021/037309.
International Search Report and Written Opinion mailed Sep. 23, 2021 in International Application No. PCT/US2021/037313.
International Search Report and Written Opinion mailed Sep. 24, 2021 in International Application No. PCT/US2021/037322.
Kovatchev et al., "Evaluating the Accuracy of Continuous Glucose-Monitoring Sensors," Diabetes Care 27:1922-1928 (2004).
Original Premarket Approval Application (Jun. 2005), 61 pgs.
Premarket Approval Application Amendment (May 2006), 89 pgs.
Reiterer et al., "Significance and Reliability of MARD for the Accuracy of CGM Systems," Journal of Diabetes Science and Technology 11(1):59-67 (2017).
Therasense Navigates Continuois Glucose Monitor PMA, Prepares for Flash, The Gray Sheet 29(37):18 (2003), 2 pgs.
Ward et al., "A Wire-Based Dual-Analyte Sensor for Glucose and Lactate: In Vitro and In Vivo Evaluation," Diabetes Technology & Therapeutics 6(3):389-401 (2004).
Website-Abbotts Continuous Blood Glucose Monitor Approval Soon, Oct. 3, 2006, 3 pgs.
Website—Children w Diabetes—Report from Diabetes Tech, Jan. 21, 2022, 3 pgs.
Website—Dexcom Leading the Way Brochure, 2009, 12 pgs.
Website—TheraSense Files Premarket Approval Application for Freestyle Navigator, Dec. 13, 2003, 3 pgs.
Wilson et al., "Introduction to the Glucose Sensing Problem," Chapter 1 (2010) 27 pgs.
U.S. Appl. No. 17/348,169, filed Jun. 15, 2021.
U.S. Appl. No. 17/347,869, filed Jun. 15, 2021.
U.S. Appl. No. 17/347,845, filed Jun. 15, 2021.
Khan et al., "Kinetics of the reduction of water-soluble colloidal MnO2 by ascorbic acid," Journal of Colloid and Interface Science 290:184-189 (2005).
U.S. Appl. No. 17/347,869, Oct. 25, 2022 Non-Final Office Action.
U.S. Appl. No. 60/490,208, filed Jul. 25, 2003, Simpson.
U.S. Appl. No. 17/347,845, Dec. 22, 2022 Non-Final Office Action.
Cho et al., "The TheraSense, Inc. Continuous Glucose Monitor: Preliminary Clinical Results from a Subcutaneous Sensor with a Wireless Connection to a Hand-Held Display/Alarm," Clinical Therapeutics/New Technology-Glucose Monitoring and Sensing, 392-P, A91 (2003).
Craston et al., "Microband Electrodes Fabricated by Screen Printing Processes: Applications in Electroanalysis," Talanta, vol. 38, No. 1, 17-26 (1991).
Brückel et al., "In Vivo Measurement of Subcutaneous Glucose Concentrations with an Enzymatic Glucose Sensor and a Wick Method", Klin Wochenschr, 67:491-495 (1989).
File Wrapper of U.S. Appl. No. 61/155,889, filed Feb. 26, 2009, 55 pages.
FreeStyle Navigator Continuous Glucose Monitoring System, User's Guide, Abbott Diabetes Care Inc., 38 pages (2008).
Guardian® Real-Time, Continuous Glucose Monitoring System, User Guide, Medtronic MiniMed, Inc., 184 pages (2006).
Mastrototaro et al., "An electroenzymatic glucose sensor fabricated on a flexible substrate", Sensors and Actuators B, 5:139-144 (1991).
U.S. Appl. No. 61/155,889, filed Feb. 26, 2009, Hoss et al.
Chen, et al., "A novel fault-tolerant sensor system for sensor drift compensation", Sensors and Actuators, A 147:623-632 (2008).
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Gerritsen, et al., "Performance of subcutaneously implanted glucose sensors for continuous monitoring", The Netherlands Journal of Medicine, 54:167-179 (1999).
Guardian® Real-Time, Continuous Glucose Monitoring System, User Guide, Medtronic MiniMed, Inc., 181 pages (2006).
Guardian® RT, Continuous Glucose Monitoring System, REF MMT-7900, User Guide, Medtronic MiniMed, 128 pages (2005).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
"Abbott Receives CE Mark for Freestyle® Libre, A Revolutionary Glucose Monitoring System for People with Diabetes," 8 pages (2023).
"FDA authorizes first fully interoperable continuous glucose monitoring system, streamlines review pathway for similar devices," FDA News Release, retrieved from https://www.fda.gov/news-events/press-announcements/fda-authorizes-first-fully-interopeable-continuous-glucose-monitoring-system-streamlines-review on Mar. 27, 2018, 3 pages.
ATTD Program, 4 pages (2009).
Boise, Interview with Dexcom CEO, Dexcom CEO Kevin Sayer Explains G6, 9 pages (2018).
Cambridge Dictionary of American English, 3 pages (2000)—Recess.
Dexcom (DXCM) Company Profile, 2017 /Q4 Earnings call transcript, 12 pages (2017).
DexCom (Dxcm) Q1 2018 Results—Earnings Call Transcript retrieved from https://seekingalpha.com/article/4168949-dexcom-dxcm-q1-2018-results-earnings-call-transcript on May 2, 2018, 4 pages.
Dexcom G6 Continuous Glucose Monitoring System User Guide, 7 pages (2020).
Dexcomg6, Continuous Glucose Monitoring System, User Guide, 22 pages (2020).
Dexcomg6, Start Here, Set up, Dexcom G6 Continuous Glucose Monitoring (CGM) System (G6), 8 pages (2019).
Dexcomg6, Using Your G6, 7 pages (2020).
Drawing Sheets for U.S. Pat. No. 10,973,443 issued Apr. 13, 2021, 2 pages.
Email communication from Sophie Hood, Jan. 24, 2023, 6 pages.
Excerpts from Expert Report of Catharine M. Lawton—Ex. 36, Spruce Point Capital Management, Does Dexcom Really Have a Future If It Can't Match Abbott's Scale? 2 pages, Mar. 21, 2019.
Hall, Interview with Kevin Sayer, President and CEO of Dexcom About The New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, (2009).
Hoss, et al., "Continuous Glucose Monitoring in Subcutaneous Tissue Using Factory-Calibrated Sensors: A Pilot Study", Diabetes Technology & Therapeutics, 12(8):591-597 (2010).

(56) References Cited

OTHER PUBLICATIONS

Hoss, et al., "Feasibility of Factory Calibration for Subcutaneous Glucose Sensors in Subjects With Diabetes", Journal of Diabetes Science and Technology, 8(1):89-94 (2014).
IEEE 100, The Authoritative Dictionary of IEEE Standards Terms, 7th Ed., 3 pages (2000).
Joint Declaration of Funderburk, et al. for U.S. Appl. No. 15/963,828, 11 pages (2020).
Letter from the Department of Health & Human Services, Food and Drug Administration to Abbott Diabetes Care, Inc. dated Mar. 12, 2008, regarding the Premarket Approval Application (PMA) for the FreeStyle Navigator Continuous Glucose Monitoring System, 7 pages.
Merriam-Webster's Collegiate Dictionary, $10^{th}$ Ed., 4 pages (1999)—Housing and recess.
Merriam-Webster's Collegiate Dictionary, $10^{th}$ Ed., 4 pages (1999)—Release and retain.
Non-Final Office Action for U.S. Appl. No. 14/884,622 dated Jun. 13, 2018, 7 pages.
Non-Final Office Action for U.S. Appl. No. 17/030,030 dated Dec. 17, 2020, 7 pages.
Notice of Allowance for U.S. Appl. No. 15/963,828 dated Mar. 3, 2021, 32 pages.
Omnipod image, Exhibit 182, 2 pages, Sep. 22, 2022.
Response to Non-Final Office Action for U.S. Appl. No. 15/963,828, filed Dec. 8, 2020, 17 pages.
Response to Restriction Requirement for U.S. Appl. No. 14/884,622, filed Apr. 5, 2018, 15 pages.
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
S&P Global Market Intelligence "DexCom, Inc. NasdaqGS:DXCM, Company Conference Presentation," 17 pages (2021).
Sayer, CGMS Changing Diabetes Management: Kevin Sayer, DIC Interview Transcript, Featuring Steve Freed, 11 pages (2019).
Sonix, Dexcom CEO—Prime Position in Our Market—Mad Money—CNBC.mp4, 4 pages (2023).
Tegnestedt, et al., "Levels and sources of sound in the intensive care unit—an observational study of three room types", Acta Anaesthesiologica Scandinavica, pp. 1-10 (2013).
The Chambers Dictionary, 4 pages (1998)—Retract.
The MiniMed Paradigm® Real-Time Insulin Pump and Continuous Glucose Monitoring System, Insulin Pump User Guide, Paradigm® 522 and 722 Insulin Pumps, Medtronic MiniMed, Inc., 25 pages (2008).
The New Oxford American Dictionary, 3 pages (2001)—Retract.
The New Penguin English Dictionary, Penguin Books, 4 pages (2000)—Recess.
U.S. Food & Drug Administration, "Deciding When to Submit a 510(k) for a Change to an Existing Device, Guidance for Industry and Food and Drug Administration Staff," 32 pages (2017).
U.S. Food & Drug Administration, "Deciding When to Submit a 510(k) for a Change to an Existing Device, Guidance for Industry and Food and Drug Administration Staff," 78 pages (2017).
Watkin, "An Introduction to Flash Glucose Monitoring," 16 pages (2013).
Webster's New College Dictionary, 2 pages (2001)—Alcove.
Webster's Third New International Dictionary, 5 pages (1993)—Retract.
FreeStyle Navigator Continuous Glucose Monitoring System, Dept of Health & Human Services, Food and Drug Administration, Mar. 12, 2008, 8 pages.
U.S. Appl. No. 17/347,845, Nov. 22, 2023 Non-Final Office Action.
U.S. Appl. No. 17/347,869, Dec. 7, 2023 Non-Final Office Action.
U.S. Appl. No. 17/347,845, Aug. 5, 2024 Non-Final Office Action.
U.S. Appl. No. 17/347,869, Jun. 10, 2024 Final Office Action.
U.S. Appl. No. 17/348,169, Jul. 5, 2024 Final Office Action.
U.S. Appl. No. 17/347,845, Mar. 6, 2025 Final Office Action.
U.S. Appl. No. 17/347,845, Apr. 9, 2024 Final Office Action.

* cited by examiner

ANALYTE SENSORS FEATURING WORKING ELECTRODE ASPERITY PLANING FOR DECREASING INTERFERENT SIGNAL

CROSS-REFERENCE TO RELATED APPLICATIONS

This application claims priority to and the benefit of U.S. Provisional Application No. 63/039,768, filed Jun. 16, 2020, which is incorporated by reference herein in its entirety.

BACKGROUND

The detection of various analytes within an individual can sometimes be vital for monitoring the condition of their health. Deviation from normal analyte levels can often be indicative of a number of physiological conditions. Glucose levels, for example, can be particularly important to detect and monitor in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Monitoring of other analytes may be desirable for other various physiological conditions. Monitoring of multiple analytes may also be desirable in some instances, particularly for comorbid conditions resulting in simultaneous dysregulation of two or more analytes in combination with one another.

Many analytes represent intriguing targets for physiological analyses, provided that a suitable detection chemistry can be identified. To this end, in vivo analyte sensors configured for assaying various physiological analytes have been developed and refined over recent years, many of which utilize enzyme-based detection strategies to facilitate detection specificity. Indeed, in vivo analyte sensors utilizing a glucose-responsive enzyme for monitoring blood glucose levels are now in common use among diabetic individuals. In vivo analyte sensors for other analytes are in various stages of development, including in vivo analyte sensors capable of monitoring multiple analytes. Poor sensitivity for low-abundance analytes may be especially problematic for some analyte sensors, particularly due to background signal arising from interaction of an interferent with a working electrode or other analyte sensing chemistry components.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 12A and 12C are not laser planed. FIGS. 12B, 12D, and 12E are laser planed, in accordance with one or more aspects of the present disclosure.

DETAILED DESCRIPTION

Figure 1:
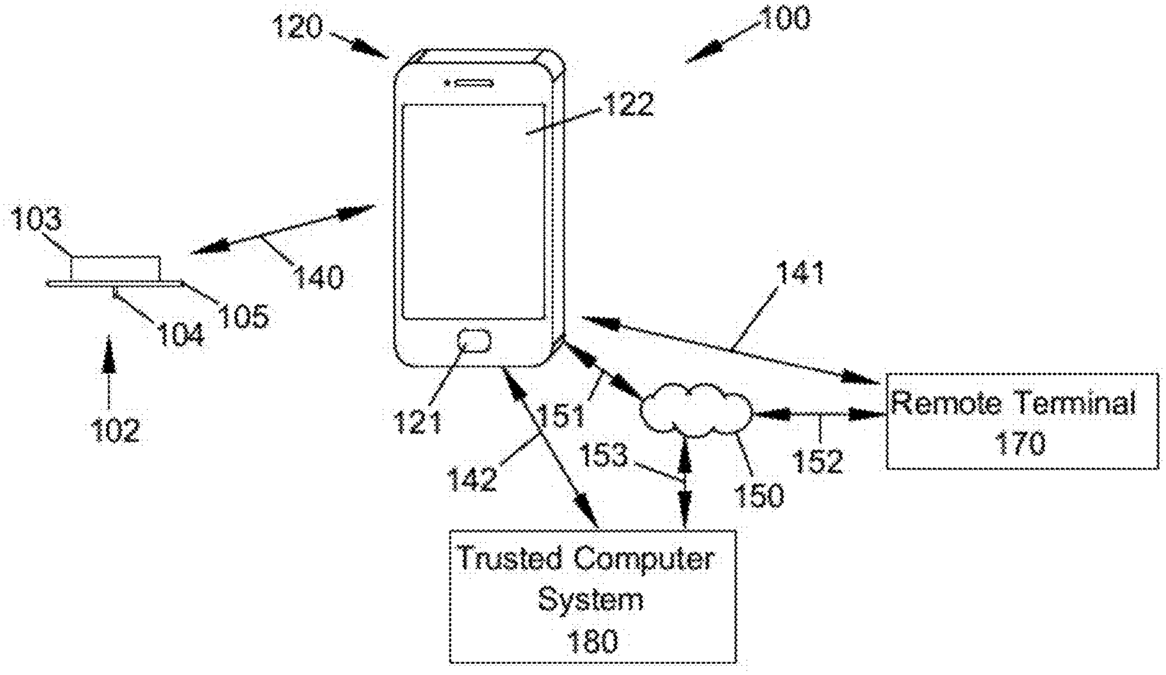
FIG. 1 shows a diagram of an illustrative sensing system that may incorporate an analyte sensor of the present disclosure.

The present disclosure generally describes analyte sensors suitable for in vivo use and, more specifically, analyte sensors featuring one or more enhancements for reducing or eliminating signals indicative of interferent species to promote improved detection sensitivity, and methods for production and use thereof.

Such enhancements may include decreasing the availability of a working electrode surface upon a sensor tail (the portion of a sensor for insertion into a tissue), particularly the availability of edges of a carbon working electrode upon a sensor tail upon which interferents may react and contribute to signal not associated with the analyte. The analyte sensors described herein comprise a sensor tail comprising at least one working electrode, particularly a carbon working electrode, and an active area disposed thereupon. A mass transport limiting membrane is then disposed upon the carbon working electrode (i.e., disposed upon both the active area and any extraneous carbon working electrode lacking the active area forming the sensor tail). Various carbon electrode asperities may exist along the edges of the carbon working electrode, where they may be insufficiently coated or are not coated at all with the mass transport limiting membrane, thereby providing a carbon surface for interferents to undergo a reaction and contribute to the measured signal at the working electrode. As used herein, the term "asperity," and grammatical variants thereof, refers to a rough edge along a surface (e.g., along a working electrode). Asperities may be in the form of a ridge along the edge of a working electrode, thereby leading to insufficient coating of a mass transport limiting membrane in this location. To reduce or eliminate such interferent signals, the present disclosure provides for singulation (ablation) of one or more edges of the carbon working electrode to remove carbon asperities therefrom, thereby affording a more uniform profile of the working electrode surface. Where the working electrode is formed from a material other than carbon, such asperities may be equally present in the composition of the particular working electrode ("electrode asperities").

Particular details and further advantages of each type of enhancement are described in further detail herein. Depending on particular needs, the analyte sensors of the present disclosure may be configured to detect one analyte or multiple analytes simultaneously or near simultaneously.

Analyte sensors employing enzyme-based detection are commonly used for assaying a single analyte, such as glucose, due to the frequent specificity of enzymes for a particular substrate or class of substrate. Analyte sensors employing both single enzymes and enzyme systems comprising multiple enzymes acting in concert may be used for this purpose. As used herein, the term "in concert," and grammatical variants thereof, refers to a coupled enzymatic reaction, in which the product of a first enzymatic reaction becomes the substrate for a second enzymatic reaction, and the second enzymatic reaction or a subsequent enzymatic reaction serves as the basis for measuring the concentration of an analyte. Moreover, a combination of enzymes and/or enzyme systems may be employed to detect more than one analyte type. Using an in vivo analyte sensor featuring an enzyme or enzyme system to promote detection may be particularly advantageous to avoid the frequent withdrawal of bodily fluid that otherwise may be required for analyte monitoring to take place.

In vivo analyte sensors monitor one or more analytes in a biological fluid of interest such as dermal fluid, interstitial fluid, plasma, blood, lymph, synovial fluid, cerebrospinal fluid, saliva, bronchoalveolar lavage, amniotic fluid, or the like. Such fluids may comprise one or more interferents that can react with the working electrode of the analyte sensor, either directly on the working electrode itself (e.g., carbon working electrode) or with one or more sensing chemistry components disposed thereupon. As used herein, the term "interferent," and grammatical variants thereof, refers to any electroactive species present that are not an analyte(s) of interest (e.g., in vivo electroactive species that are not an analyte(s) of interest). Examples include, but are not limited to, ascorbic acid (vitamin C and also referred to as ascorbate), glutathione, uric acid, paracetamol (acetaminophen), isoniazid, salicylate, and the like, and any combination thereof. The reaction of these interferents with the working electrode can create an electrochemical signal that is inseparable or not easily separable from signal originating from the analyte of interest, which may complicate the accurate detection of such analytes, particularly those in low-abundance (e.g., low-to sub-millimolar concentrations). The electrochemical signal generated by an interferent may be particularly problematic as the signal from the interferent becomes closer in magnitude to that of the signal from the target analyte. This may occur, for example, when the concentration of the interferent approaches or exceeds the concentration of the analyte of interest. Some interferents are ubiquitous in vivo and are not easily avoided. Therefore, techniques to minimize their influence during in vivo analyses may be highly desirable.

The present disclosure provides analyte sensor enhancements that, either alone or in combination with other enhancements, may improve detection sensitivity for both single analytes and multiple analytes in combination with one another, as explained in further detail hereinbelow. Namely, the present disclosure provides analyte sensors having reduced carbon working electrode edge asperities that may afford decreased background signal resulting from in vivo interferents. Although certain aspects of the present disclosure are directed to enhancement of carbon working electrodes, it is to be appreciated that other types of electrodes may be similarly enhanced according to the disclosure herein. Electrode types that may be enhanced through use of the disclosure herein also include gold, platinum, PEDOT, and the like.

Before describing the analyte sensors of the present disclosure and their enhancements in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure. As shown, sensing system 100 includes sensor control device 102 and reader device 120 that are configured to communicate with one another over local communication path or link 140, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances.

Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety.

Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Alternately, sensor 104 may be adapted to penetrate the epidermis. Still further alternately, sensor 104 may be disposed superficially and not penetrate a tissue, such as when assaying one or more analytes in perspiration upon the skin. Sensor 104 may comprise a sensor tail of sufficient length for insertion to a desired depth in a given tissue. The sensor tail may comprise at least one working electrode and an active area comprising an enzyme or enzyme system configured for assaying one or more analytes of interest.

A counter electrode may be present in combination with the at least one working electrode, optionally in further combination with a reference electrode. Particular electrode configurations upon the sensor tail are described in more detail below in reference to FIGS. 2A-4. One or more enzymes in the active area may be covalently bonded to a polymer comprising the active area, according to various embodiments. Alternately, enzymes may be non-covalently associated within the active area, such as through encapsulation or physical entrainment. The one or more analytes may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine analyte concentrations in vivo. It is to be appreciated, however, that the entirety of sensor control device 102 may have one or more various configurations permitting full transplantation beneath tissue and into one or more body fluids for assaying one or more analytes of interest, without departing from the scope of the present disclosure.

Referring again to FIG. 1, sensor 104 may automatically forward data to reader device 120. For example, analyte concentration data may be communicated automatically and periodically, such as at a certain frequency as data is obtained or after a certain time period has passed, with the data being stored in a memory until transmittal (e.g., every minute, five minutes, or other predetermined time period), such as by BLUETOOTH® or BLUETOOTH® Low Energy protocols. Data associated with different analytes may be forwarded at the same frequency or different frequencies and/or using the same or different communication protocols. In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time, automatically or non-automatically. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp, or a combination thereof. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications. For example, needles having a cross-sectional diameter ranging from about 300 microns to about 400 microns may be used.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle may be subsequently withdrawn after facilitating sensor insertion.

Figure 2A:
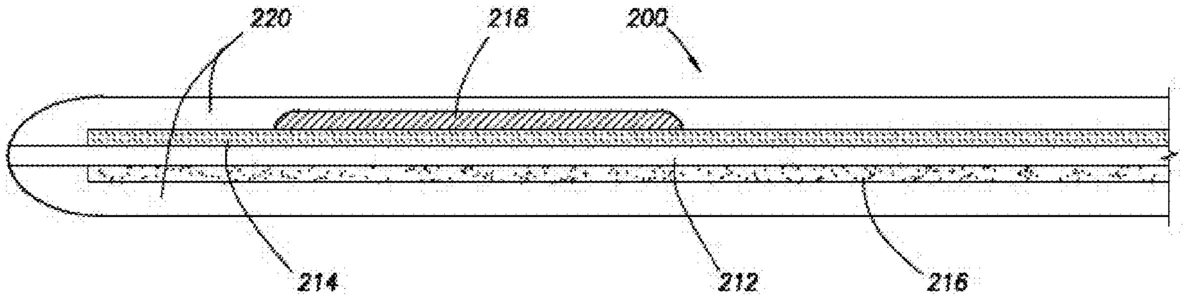
FIGS. 2A-2C show cross-sectional diagrams of analyte sensors comprising a single active area.
Figure 2B:
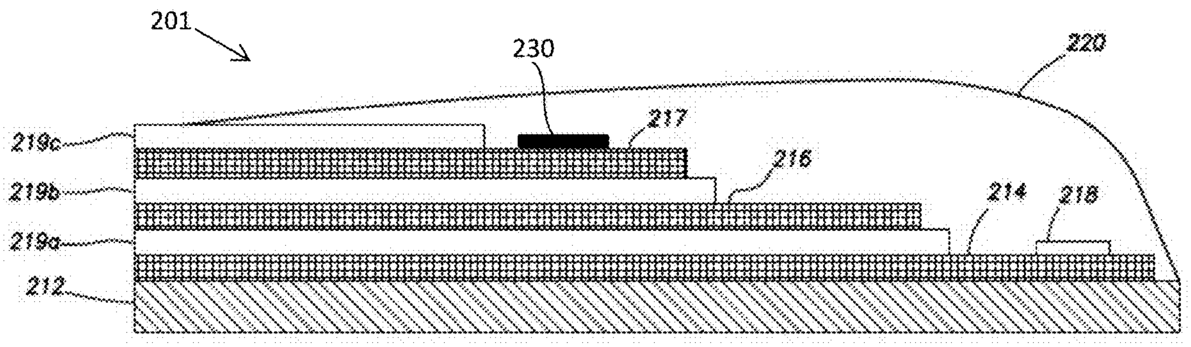
Figure 2C:
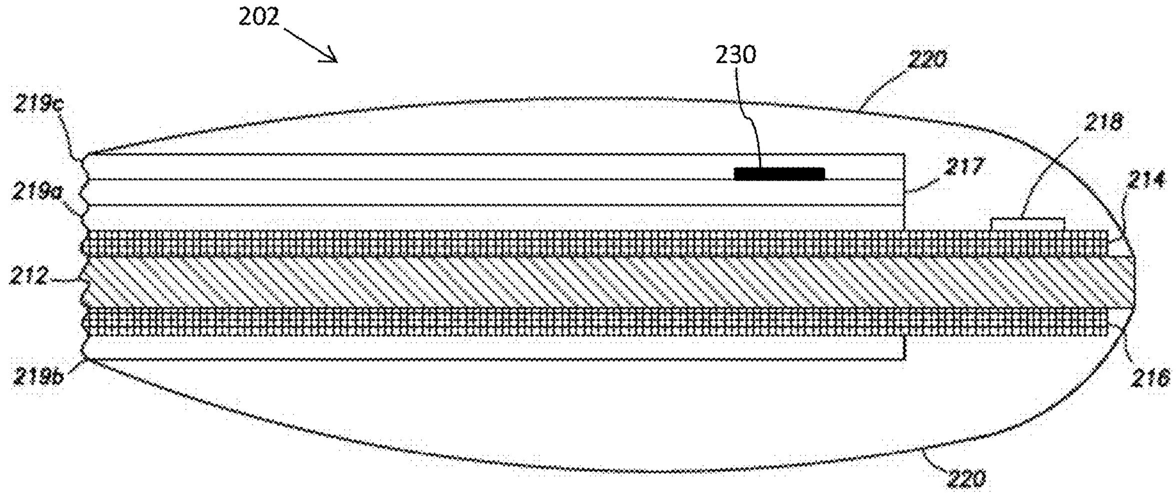

Sensor configurations featuring a single active area that is configured for detection of a corresponding single analyte may employ two-electrode or three-electrode detection motifs, as described further herein in reference to FIGS. 2A-2C. Sensor configurations featuring two different active areas for detection of separate analytes, either upon separate working electrodes or upon the same working electrode, are described separately thereafter in reference to FIGS. 3A-4. Sensor configurations having multiple working electrodes may be particularly advantageous for incorporating two different active areas within the same sensor tail, since the signal contribution from each active area may be determined more readily through separate interrogation of each working electrode. Each active area may be overcoated with a mass transport limiting membrane of the same or different composition.

When a single working electrode is present in an analyte sensor, three-electrode sensor configurations may comprise a working electrode, a counter electrode, and a reference electrode. Related two-electrode sensor configurations may comprise a working electrode and a second electrode, in which the second electrode may function as both a counter electrode and a reference electrode (i.e., a counter/reference electrode). The various electrodes may be at least partially stacked (layered) upon one another and/or laterally spaced apart from one another upon the sensor tail. In any of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

Any of the working electrode configurations described hereinafter may benefit from the further disclosure below directed to decreasing the availability of edge asperities of the working electrode upon the sensor tail.

FIG. 2A shows a diagram of an illustrative two-electrode analyte sensor configuration, which is compatible for use in the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. Active area 218 may comprise multiple spots or a single contiguous spot configured for detection of an analyte, as discussed further herein.

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 (i.e., membrane 220 is a mass transport limiting membrane having some permeability for the analyte of interest). The composition and thickness of membrane 220 may vary to promote a desired analyte flux to active area 218, thereby providing a desired signal intensity and stability. Analyte sensor 200 may be operable for assaying an analyte by any of coulometric, amperometric, voltammetric, or potentiometric electrochemical detection techniques.

FIGS. 2B and 2C show diagrams of illustrative three-electrode analyte sensor configurations, which are also compatible for use in the disclosure herein. Three-electrode analyte sensor configurations may be similar to that shown for analyte sensor 200 in FIG. 2A, except for the inclusion of additional electrode 217 in analyte sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219*a*, 219*b*, and 219*c* separate electrodes 214, 216, and 217 from one another and provide electrical isolation. Alternately, at least one of electrodes 214, 216, and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 2A, active area 218 in analyte sensors 201 and 202 may comprise multiple spots or a single spot. Additionally, analyte sensors 201 and 202 may likewise be operable for assaying an analyte by any of coulometric, amperometric, voltammetric, or potentiometric electrochemical detection techniques.

Like analyte sensor 200, membrane 220 may also overcoat active area 218, as well as other sensor components, in analyte sensors 201 and 202, thereby serving as a mass transport limiting membrane. Additional electrode 217 may be overcoated with membrane 220 in some embodiments. Membrane 220 may again be produced through dip coating or in situ photopolymerization and vary compositionally or be the same compositionally at different locations. Although FIGS. 2B and 2C have depicted all of electrodes 214, 216, and 217 as being overcoated with membrane 220, it is to be recognized that only working electrode 214 or active area 218 may be overcoated in some embodiments. Moreover, the thickness of membrane 220 at each of electrodes 214, 216, and 217 may be the same or different. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

Figure 3A:
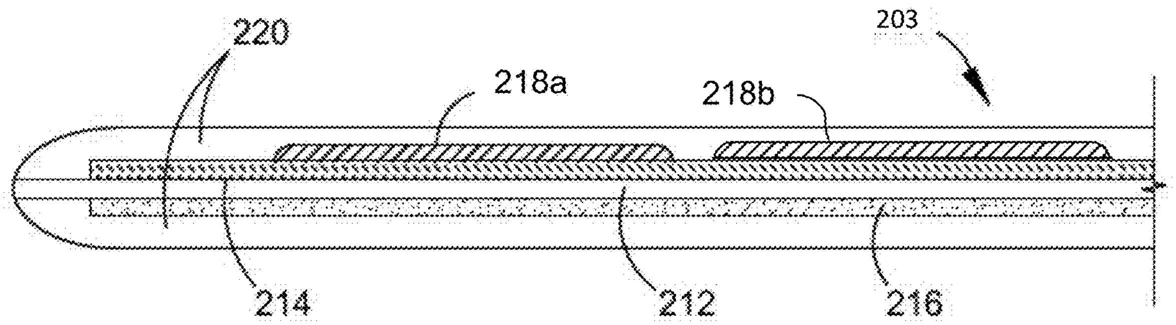
FIGS. 3A-3C show cross-sectional diagrams of analyte sensors comprising two active areas.

FIG. 3A shows an illustrative configuration for sensor 203 having a single working electrode with two different active areas disposed thereon. FIG. 3A is similar to FIG. 2A, except for the presence of two active areas upon working electrode 214: first active area 218*a* and second active area 218*b*, which are responsive to different analytes and are laterally spaced apart from one another upon the surface of working electrode 214. Active areas 218*a* and 218*b* may comprise multiple spots or a single spot configured for detection of each analyte. The composition of membrane 220 may vary or be compositionally the same at active areas 218*a* and 218*b*. First active area 218*a* and second active area 218*b* may be configured to detect their corresponding analytes at working electrode potentials that differ from one another, as discussed further below.

Figure 3B:
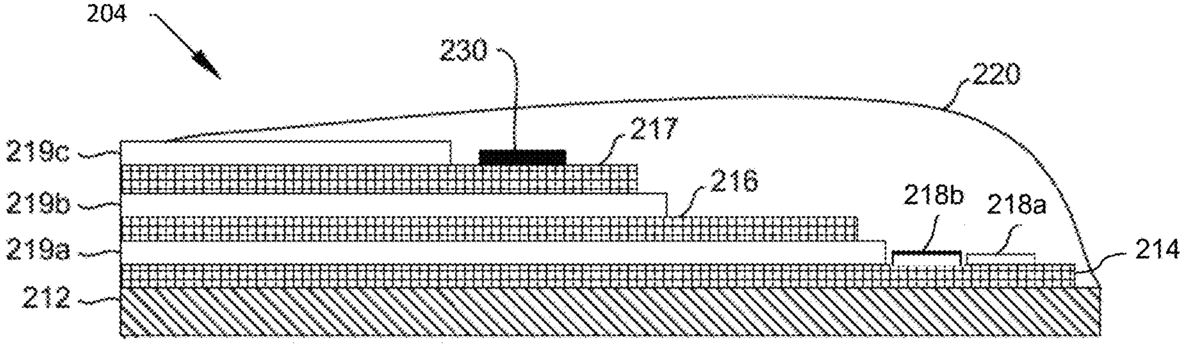
Figure 3C:
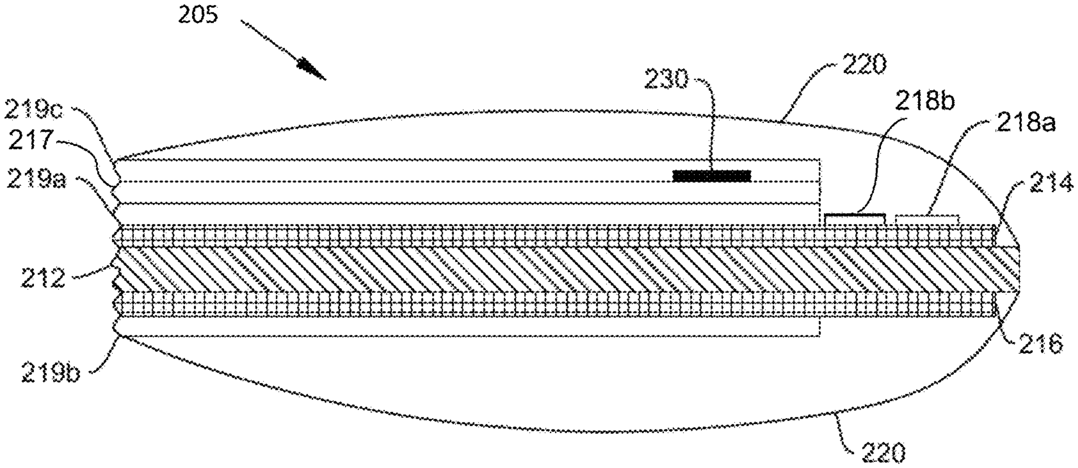

FIGS. 3B and 3C show cross-sectional diagrams of illustrative three-electrode sensor configurations for sensors 204 and 205, respectively, each featuring a single working electrode having first active area 218*a* and second active area 218*b* disposed thereon. FIGS. 3B and 3C are otherwise similar to FIGS. 2B and 2C and may be better understood by reference thereto. As with FIG. 3A, the composition of membrane 220 may vary or be compositionally the same at active areas 218*a* and 218*b*.

Figure 4:
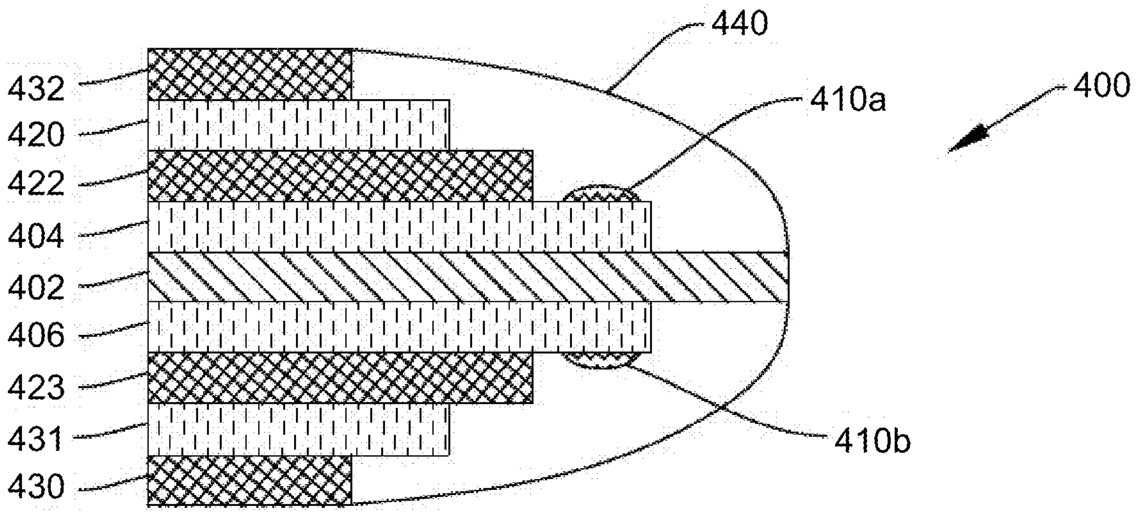
FIG. 4 shows a cross-sectional diagram of an analyte sensor comprising two working electrodes, each having an active area present thereon.

FIG. 4 shows a cross-sectional diagram of an illustrative analyte sensor configuration having two working electrodes, a reference electrode, and a counter electrode, which is compatible for use in the disclosure herein. As shown, analyte sensor 400 includes working electrodes 404 and 406 disposed upon opposite faces of substrate 402. First active area 410*a* is disposed upon the surface of working electrode 404, and second active area 410*b* is disposed upon the surface of working electrode 406. Counter electrode 420 is electrically isolated from working electrode 404 by dielectric layer 422, and reference electrode 431 is electrically isolated from working electrode 406 by dielectric layer 423. Outer dielectric layers 430 and 432 are positioned upon reference electrode 431 and counter electrode 420, respectively. Membrane 440 may overcoat at least active areas 410*a* and 410*b*, according to various embodiments, with other components of analyte sensor 400 or the entirety of analyte sensor 400 optionally being overcoated with membrane 440 as well. Again, membrane 440 may vary compositionally at active areas 410*a* and 410*b*, if needed, in order to afford suitable permeability values for differentially regulating the analyte flux at each location.

Alternative sensor configurations having multiple working electrodes and differing from the configuration shown in FIG. 4 may feature a counter/reference electrode instead of separate counter and reference electrodes 420, 431, and/or feature layer and/or membrane arrangements varying from those expressly depicted. For example, the positioning of counter electrode 420 and reference electrode 431 may be reversed from that depicted in FIG. 4. In addition, working electrodes 404 and 406 need not necessarily reside upon opposing faces of substrate 402 in the manner shown in FIG. 4.

A carbon working electrode may suitably comprise the working electrode(s) in any of the analyte sensors disclosed herein. While carbon working electrodes are very commonly employed in electrochemical detection, use thereof in electrochemical sensing is not without difficulties. In particular, current related to an analyte of interest only results when an active area interacts with an analyte and transfers electrons to the portion of the carbon working electrode adjacent to the active area. Bodily fluid containing an analyte of interest also interacts with a carbon surface of the carbon working electrode not overcoated with an active area and does not contribute to the analyte signal, since there is no enzyme or enzyme system present at these locations to facilitate electron transfer from the analyte to the working electrode. Interferents may, however, undergo oxidation at portions of the working electrode lacking an active area and contribute background to the overall signal. Thus, carbon working electrodes with an extraneous (or "exposed") carbon area upon the electrode surface do not meaningfully contribute to the analyte signal and may lead to contributory background signals in some cases. Other electrodes having an excessive surface area not directly detecting an analyte of interest may experience similar background signals and may be enhanced through modification of the disclosure herein.

Although various interferents may interact with the working electrode of the analyte sensors described herein, ascorbic acid is one example of an interferent commonly present in biological fluids that may generate a background signal at a carbon working electrode. For example, ascorbic acid oxidizes at the working electrode to produce dehydroascorbic acid. Various embodiments of the present disclosure will be described herein with reference to the interferent being ascorbic acid; however, it is to be understood that the embodiments and analyte sensor configurations described herein are equally applicable to other interferents (electroactive species within a bodily fluid having an analyte of interest).

Figure 5:
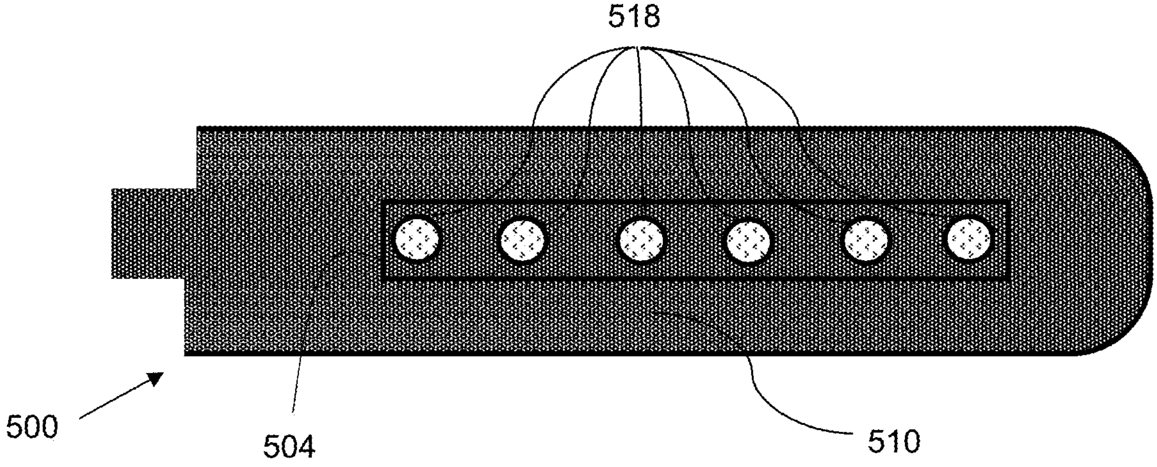
FIG. 5 is a diagram showing a top view of a conventional carbon working electrode having an active area thereon.

As provided above, the active area described herein may be a single sensing layer, a sensing layer having multiple sensing spots, or a sensing layer having multiple sensing spots compressed together and thus representing essentially a single sensing layer. Referring now to FIG. 5, illustrated is a top view of conventional carbon working electrode 500 having an active area 504 disposed thereon comprising multiple sensing spots 518. Only portions of carbon working electrode 500 comprising the sensing spots 518 contribute signal associated with an analyte of interest when the analyte interacts with the active area 504. Although carbon working electrode 500 shows six sensing spots 518 within the active area 504, it is to be appreciated that fewer or greater than six sensing spots 518 may be included upon carbon working electrode 500, without departing from the scope of the present disclosure. Extraneous carbon area 510 is not directly overlaid with sensing spots 518 and does not contribute signal associated with the analyte but may generate a background signal associated with one or more interferents. Accordingly, the oxidation of interferents at carbon working electrode 500 is proportional to the area of extraneous carbon area 510 available for interaction with the interferents. Indeed, the oxidation of ascorbic acid at carbon working electrode 500 scales roughly linearly with the area of available extraneous carbon area 510.

As shown, the active area 504 is discontinuous and in the form of multiple sensing spots 518. As defined herein, the term "discontiguous," and grammatical variants thereof, means that any single spot (sensing element) does not share an edge or boundary (e.g., is not touching) an adjacent spot.

The sensor tails described in the present disclosure comprising the carbon working electrode 500 may be prepared upon a template substrate material (see FIGS. 2A-2B, 3A-3C, 4) along with additional layered elements of the sensor tail (e.g., dielectric materials, other electrodes, and the like). During sensor fabrication, the sensor tail comprising the carbon working electrode 500 is thereafter singulated by one or more means. Singulation may be achieved by one or more cutting or separation protocols including, but not limited to, laser singulation, slitting, shearing, punching, and the like. Singulation of the sensor tails may be performed before or after application of the active area upon the carbon working electrode 500 toward the distal tip of the sensor tail (i.e., the portion of the sensor tail that will be inserted deepest into a tissue). As used herein, the distal "tip" of the sensor tail is referred to as the most distal edge of a sensor tail, or that portion that is most deeply inserted into a tissue.

One or more portions of the sensor tail are laser singulated, typically requiring multiple laser passes, to cut the sensor tail into the desired shape. At the tip of the sensor tail comprises at least a portion of the working electrode and the active area. Typically, the laser singulated sensor tails have a width in the range of about 50 μm to about 800 μm and a length of about 1 mm to about 20 mm, such as a width in the range of about 100 μm to about 500 μm and a length of about 3 mm to about 10 mm, encompassing any value and subset therebetween and in which the upper and lower limits are separable. Generally, the distal portion of the sensor tail accounts for a distal length of about 0.1 mm to about 10 mm, such as about 0.1 mm to about 5 mm, encompassing any value and subset therebetween and in which the upper and lower limits are separable. After laser singulation, a mass transport limiting membrane is deposited upon at least the sensor tip.

Prior to disposing the mass transport limiting membrane, carbon asperities may be present along the edges of the carbon electrode due to the laser singulation process. These carbon asperities provide a surface upon which interferents may react and contribute background signal to an analyte sensor.

Laser singulation of a carbon working electrode may result in the formation of carbon asperities having widths of about 75 μm or less, such as in the range of about 1 μm to about 75 μm, or about 5 μm to about 50 or about 10 μm to about 30 μm, encompassing any value and subset therebetween and in which the upper and lower limits are separable. Further, these carbon asperities may have a height of about 50 μm or less, or about 20 μm or less, such as in the range of about 1 μm to about 50 μm, or about 1 μm to about 30 μm, or about 1 μm to about 20 μm, or about 2 μm to about 10 μm, as described hereinbelow in greater detail, encompassing any value and subset therebetween and in which the upper and lower limits are separable. Accordingly, these carbon asperities may provide substantial area with which interferents may interact. In addition, the asperities can contribute to inconsistent coverage (thickness) of a mass transport limiting membrane. These carbon asperities may be reduced or removed by one or more laser planing methods, as described hereinbelow.

Figure 6A:
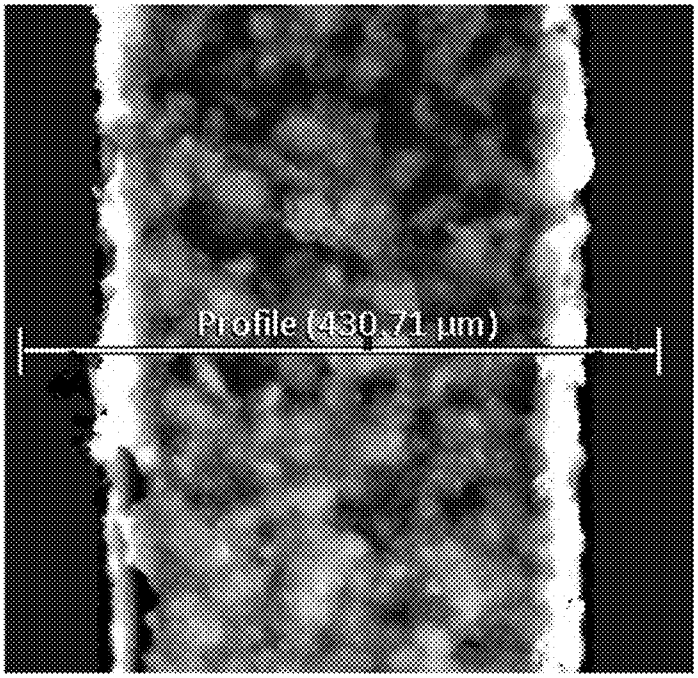
FIG. 6A shows a photograph of a top view of a working electrode having no membrane disposed thereon.
Figure 6B:
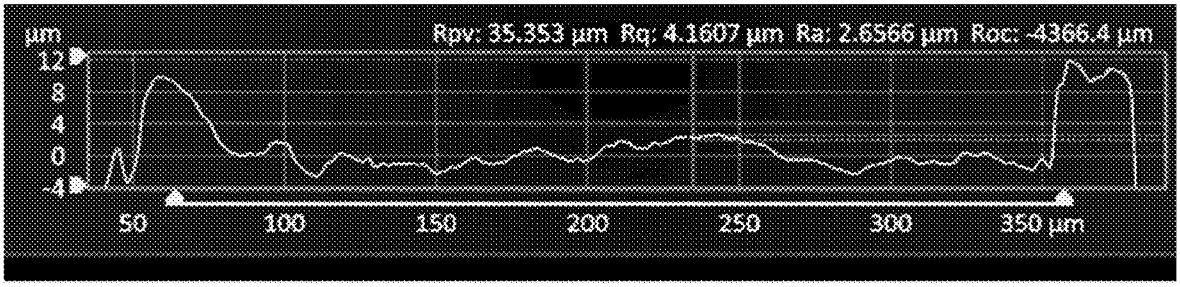
FIG. 6B is a depth profile along the line indicated in FIG. 6A.

Referring first to FIG. 6A, and prior to any laser planing to reduce or remove carbon asperities in accordance with the present disclosure, illustrated is a close up of an example of a laser singulated carbon working electrode for use as at least a portion of a sensor tail, in which the carbon working electrode has no mass transport limited membrane deposited thereon. Electrodes cut into their desired shape by other means may have asperities of a similar size. Carbon asperities are apparent along the edges of the working electrode with which interferents may react. FIG. 6B shows a depth profile along the line indicated in FIG. 6A, evaluated along the identified 430.71 μm profile width. The 3D optical profile was obtained using a ZEGAGE™ 3D Optical Profiler, ZYGOO® Corporation (Middlefield, CT). As shown in FIG. 6B, carbon asperities along the singulation (ablation) edges of the example singulated sensor tail are up to about 30 μm wide and up to about 10 μm in height.

A mass transport limiting membrane may reduce or prevent interferent access to extraneous carbon areas (e.g., extraneous carbon area 510 of FIG. 5). When disposed upon a laser singulated carbon working electrode (and an active area thereupon), the thickness of the membrane varies across the width of the working electrode when significant asperities are present. Typically, the membrane is thinnest along the edges of the electrode, which is also where the carbon asperities are located. Accordingly, even when a membrane is present, the carbon asperities may not be sufficiently coated with the membrane to adequately reduce or prevent interferent interaction with the carbon asperities.

Figure 7A:
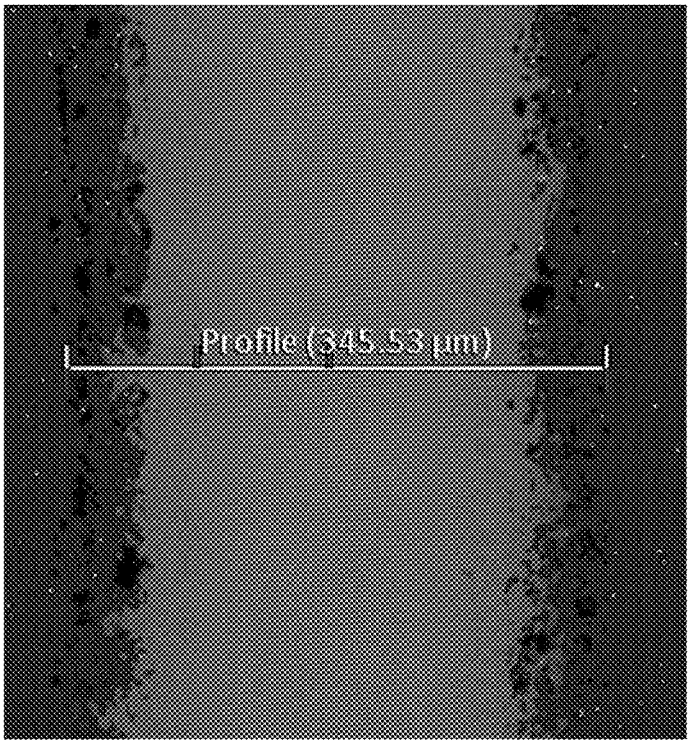
FIG. 7A shows a photograph of a top view of a working electrode having membrane disposed thereon.
Figure 7B:
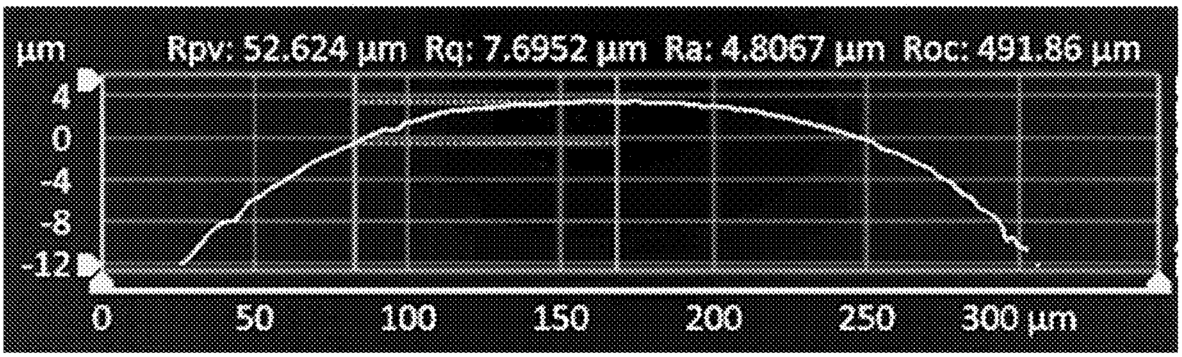
FIG. 7B is a depth profile along the line indicated in FIG. 7A.

Referring to FIG. 7A, and prior to any laser planing to reduce or remove carbon asperities in accordance with the present disclosure, illustrated is a close up of an example laser singulated carbon working electrode having a mass transport limited membrane deposited thereon. FIG. 7B shows a depth profile along the line indicated in FIG. 7A, evaluated along the identified 345.53 μm profile width. The 3D optical profile was obtained using a ZEGAGE™ 3D Optical Profiler, ZYGOO® Corporation (Middlefield, CT). As shown in FIG. 7B, the membrane is considerably thinner along the singulation ridges of the carbon working electrode.

The present disclosure provide methods and analyte sensors in which carbon working electrodes for use in forming a sensor tail are planed by one or more single- or multi-pass laser planing cuts. In some embodiments, a single-pass laser planing method is used in which the laser depth is set to less than the thickness of the working electrode. For example, the laser planing may remove the top portions of the carbon layer, such as the top about 50% of the carbon layer. The carbon layer is typically in the range of 5 μm to about 20 μm (without asperities); in some embodiments, about 5 μm to about 10 μm (e.g., about 20%, 30%, 40%, 50%, 60%, or 70%, up to 100%) may be removed therefrom (e.g., see FIG. 9C). Laser planing according to the disclosure herein may remove or decrease the prominence of asperities.

In some embodiments, greater than 1, such as less than about 20 (or about 15, or about 10), single-pass laser planing cuts may be made, each progressively closer to the midline length of the working electrode to reduce or eliminate the carbon asperities. In such a way, initial laser planing cuts may be made at the outermost location of any single carbon asperity and subsequent laser planing cuts may be made toward the midline length of the working electrode to create a milled edge, which may be a stepped edge of approximately 90° or a beveled edge (i.e., an edge that is not perpendicular to the faces of the electrode) if, for example, the most proximal laser planing cut toward the midline of the electrode does not result in a true 90° angle (see FIG. 8, laser planing cut (edge) 810 shown as a sloped edge rather than a shear 90° angle edge). For example, in one embodiment, about 1 to about 20, such as about 2 to about 10, single-pass laser planing cuts may be made, each having a distance apart between about 0.1 μm to about 200 μm, such as about 1 μm to about 100 μm, encompassing any value and subset therebetween and in which the upper and lower limits are separable. Selection of the particular number of laser planing passes and their distance apart may be based on a number of factors including, but not limited to, the shape and size of the carbon asperities, the length and width of the working electrode, the coverage profile of any membrane disposed thereupon, and the like, and any combination thereof.

Figure 8:
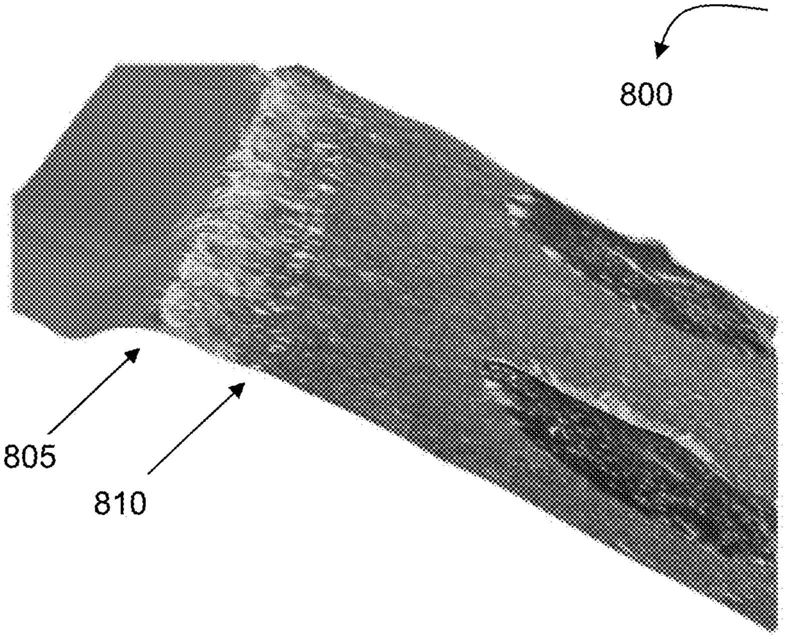
FIG. 8 is a photograph showing a 3D view of a laser planed working electrode, in accordance with one or more aspects of the present disclosure.

Laser planing may be preferentially used to remove at least about 5% up to about 100% of the total carbon asperity area from a singulated sensor tail comprising a carbon working electrode, or about encompassing any value and subset therebetween. In some embodiments, up to 100% of the carbon asperities are removed, or about 5% to about 75%, or about 5% to about 50%, or about 5% to about 25% of the total carbon asperity area are removed, encompassing any value and subset therebetween and in which the upper and lower limits are separable. In preferred embodiments, at least about 50% of the carbon asperities total area is removed. The particular amount of carbon asperity removal may be based on a number of factors including, but not limited to, the density, shape, and size of the carbon asperities, the concentration of analyte of interest compared to the concentration of interferent available within the bodily fluid being assayed and the like, and any combination thereof. FIG. 8 shows a photograph of an edge of a sensor tail 800 showing laser singulation cut (ridge) 805 and laser planing cut (edge) 810 recessed from the edge of the sensor tail to remove a portion of the edge of a carbon working electrode (the carbon or electrode layer), in accordance with one or more embodiments of the present disclosure. That is, the laser planing cut 810 is directed to reducing the carbon asperities along the upper or top portion of the carbon electrode (where the active area resides, for example), while a thinner portion of the working electrode remains along an outer perimeter (and at the opposite portion of the electrode, which does not comprise the active area).

Active areas within any of the analyte sensors disclosed herein may comprise one or more analyte-responsive enzymes, either acting alone or in concert within an enzyme system. One or more enzymes may be covalently bonded to a polymer comprising the active area, as can one or more electron transfer agents located within the active area.

Examples of suitable polymers within each active area may include poly(4-vinylpyridine) and poly(N-vinylimidazole) or a copolymer thereof, for example, in which quaternized pyridine and imidazole groups serve as a point of attachment for an electron transfer agent or enzyme(s). Other suitable polymers that may be present in the active area include, but are not limited to, those described in U.S. Pat. No. 6,605,200, incorporated herein by reference in its entirety, such as poly(acrylic acid), styrene/maleic anhydride copolymer, methylvinylether/maleic anhydride copolymer (GANTREZ polymer), poly(vinylbenzylchloride), poly(allylamine), polylysine, poly(4-vinylpyridine) quaternized with carboxypentyl groups, and poly(sodium 4-styrene sulfonate).

Enzymes covalently bound to the polymer in the active areas that are capable of promoting analyte detection are not believed to be particularly limited. Suitable enzymes may include those capable of detecting glucose, lactate, ketones, creatinine, or the like. Any of these analytes may be detected in combination with one another in analyte sensors capable of detecting multiple analytes. Suitable enzymes and enzyme systems for detecting these analytes are described hereinafter.

In some embodiments, the analyte sensors may comprise a glucose-responsive active area comprising a glucose-responsive enzyme disposed upon the sensor tail. Suitable glucose-responsive enzymes may include, for example, glucose oxidase or a glucose dehydrogenase (e.g., pyrroloquinoline quinone (PQQ) or a cofactor-dependent glucose dehydrogenase, such as flavine adenine dinucleotide (FAD)-dependent glucose dehydrogenase or nicotinamide adenine dinucleotide (NAD)-dependent glucose dehydrogenase). Glucose oxidase and glucose dehydrogenase are differentiated by their ability to utilize oxygen as an electron acceptor when oxidizing glucose; glucose oxidase may utilize oxygen as an electron acceptor, whereas glucose dehydrogenases transfer electrons to natural or artificial electron acceptors, such as an enzyme cofactor. Glucose oxidase or glucose dehydrogenase may be used to promote detection. Both glucose oxidase and glucose dehydrogenase may be covalently bonded to a polymer comprising the glucose-responsive active area and exchange electrons with an electron transfer agent (e.g., an osmium (Os) complex or similar transition metal complex), which may also be covalently bonded to the polymer. Suitable electron transfer agents are described in further detail below. Glucose oxidase may directly exchange electrons with the electron transfer agent, whereas glucose dehydrogenase may utilize a cofactor to promote electron exchange with the electron transfer agent. FAD cofactor may directly exchange electrons with the electron transfer agent. NAD cofactor, in contrast, may utilize diaphorase to facilitate electron transfer from the cofactor to the electron transfer agent. Further details concerning glucose-responsive active areas incorporating glucose oxidase or glucose dehydrogenase, as well as glucose detection therewith, may be found in commonly owned U.S. Pat. No. 8,268,143, for example.

In some embodiments, the active areas of the present disclosure may be configured for detecting ketones. Additional details concerning enzyme systems responsive to ketones may be found in commonly owned U.S. patent application Ser. No. 16/774,835 entitled "Analyte Sensors and Sensing Methods Featuring Dual Detection of Glucose and Ketones," filed on Jan. 28, 2020, and published as U.S. Patent Application Publication 2020/0237275, incorporated herein by reference in its entirety. In such systems, β-hydroxybutyrate serves as a surrogate for ketones formed in vivo, which undergoes a reaction with an enzyme system comprising β-hydroxybutyrate dehydrogenase (HBDH) and diaphorase to facilitate ketones detection within a ketones-responsive active area disposed upon the surface of at least one working electrode, as described further herein. Within the ketones-responsive active area, β-hydroxybutyrate dehydrogenase may convert β-hydroxybutyrate and oxidized nicotinamide adenine dinucleotide ($NAD^+$) into acetoacetate and reduced nicotinamide adenine dinucleotide (NADH), respectively. It is to be understood that the term "nicotinamide adenine dinucleotide (NAD)" includes a phosphate-bound form of the foregoing enzyme cofactors. That is, use of the term "NAD" herein refers to both $NAD^+$ phosphate and NADH phosphate, specifically a diphosphate linking the two nucleotides, one containing an adenine nucleobase and the other containing a nicotinamide nucleobase. The $NAD^+$/NADH enzyme cofactor aids in promoting the concerted enzymatic reactions disclosed herein. Once formed, NADH may undergo oxidation under diaphorase mediation, with the electrons transferred during this process providing the basis for ketone detection at the working electrode. Thus, there is a 1:1 molar correspondence between the amount of electrons transferred to the working electrode and the amount of β-hydroxybutyrate converted. Transfer of the electrons to the working electrode may take place under further mediation of an electron transfer agent, such as an osmium (Os) compound or similar transition metal complex, as described in additional detail below. Albumin may further be present as a stabilizer within the active area. The β-hydroxybutyrate dehydrogenase and the diaphorase may be covalently bonded to a polymer comprising the ketones-responsive active area. The $NAD^+$ may or may not be covalently bonded to the polymer, but if the $NAD^+$ is not covalently bonded, it may be physically retained within the ketones-responsive active area, such as with a mass transport limiting membrane overcoating the ketones-responsive active area, wherein the mass transport limiting membrane is also permeable to ketones.

Other suitable chemistries for enzymatically detecting ketones may be utilized in accordance with the embodiments of the present disclosure. For example, β-hydroxybutyrate dehydrogenase (HBDH) may again convert β-hydroxybutyrate and $NAD^+$ into acetoacetate and NADH, respectively. Instead of electron transfer to the working electrode being completed by diaphorase and a suitable redox mediator, the reduced form of NADH oxidase (NADHOx (Red)) undergoes a reaction to form the corresponding oxidized form (NADHOx (Ox)). NADHOx (Red) may then reform through a reaction with molecular oxygen to produce superoxide, which may undergo subsequent conversion to hydrogen peroxide under superoxide dismutase (SOD) mediation. The hydrogen peroxide may then undergo oxidation at the working electrode to provide a signal that may be correlated to the amount of ketones that were initially present. The SOD may be covalently bonded to a polymer in the ketones-responsive active area, according to various embodiments. The β-hydroxybutyrate dehydrogenase and the NADH oxidase may be covalently bonded to a polymer in the ketones-responsive active area, and the $NAD^+$ may or may not be covalently bonded to a polymer in the ketones-responsive active area. If the $NAD^+$ is not covalently bonded, it may be physically retained within the ketones-responsive active area, with a membrane polymer promoting retention of the $NAD^+$ within the ketones-responsive active area. There is again a 1:1 molar correspondence between the amount of electrons transferred to the working electrode and the amount of β-hydroxybutyrate converted, thereby providing the basis for ketones detection.

Another enzymatic detection chemistry for ketones may utilize β-hydroxybutyrate dehydrogenase (HBDH) to convert β-hydroxybutyrate and $NAD^+$ into acetoacetate and NADH, respectively. The electron transfer cycle in this case is completed by oxidation of NADH by 1,10-phenanthroline-5,6-dione to reform $NAD^+$, wherein the 1,10-phenanthroline-5,6-dione subsequently transfers electrons to the working electrode. The 1,10-phenanthroline-5,6-dione may or may not be covalently bonded to a polymer within the ketones-responsive active area. The β-hydroxybutyrate dehydrogenase may be covalently bonded to a polymer in the ketones-responsive active area, and the $NAD^+$ may or may not be covalently bonded to a polymer in the ketones-responsive active area. Inclusion of an albumin in the active area may provide a surprising improvement in response stability. A suitable membrane polymer may promote retention of the $NAD^+$ within the ketones-responsive active area. There is again a 1:1 molar correspondence between the amount of electrons transferred to the working electrode and the amount of β-hydroxybutyrate converted, thereby providing the basis for ketones detection.

In some embodiments, the analyte sensors may further comprise a creatinine-responsive active area comprising an enzyme system that operates in concert to facilitate detection of creatinine. Creatinine may react reversibly and hydrolytically in the presence of creatinine amidohydrolase (CNH) to form creatine. Creatine, in turn, may undergo catalytic hydrolysis in the presence of creatine amidohydrolase (CRH) to form sarcosine. Neither of these reactions produces a flow of electrons (e.g., oxidation or reduction) to provide a basis for electrochemical detection of the creatinine. The sarcosine produced via hydrolysis of creatine may undergo oxidation in the presence of the oxidized form of sarcosine oxidase (SOX-ox) to form glycine and formaldehyde, thereby generating the reduced form of sarcosine oxidase (SOX-red) in the process. Hydrogen peroxide also may be generated in the presence of oxygen. The reduced form of sarcosine oxidase, in turn, may then undergo re-oxidation in the presence of the oxidized form of an electron transfer agent (e.g., an Os(III) complex), thereby producing the corresponding reduced form of the electron transfer agent (e.g., an Os(II) complex) and delivering a flow of electrons to the working electrode.

Oxygen may interfere with the concerted sequence of reactions used to detect creatinine in accordance with the disclosure above. Specifically, the reduced form of sarcosine oxidase may undergo a reaction with oxygen to reform the corresponding oxidized form of this enzyme but without exchanging electrons with the electron transfer agent. Although the enzymes all remain active when the reaction with oxygen occurs, no electrons flow to the working electrode. Without being bound by theory or mechanism, the competing reaction with oxygen is believed to result from kinetic effects. That is, oxidation of the reduced form of sarcosine oxidase with oxygen is believed to occur faster than does oxidation promoted by the electron transfer agent. Hydrogen peroxide is also formed in the presence of the oxygen.

The desired reaction pathway for facilitating detection of creatinine may be encouraged by including an oxygen scavenger in proximity to the enzyme system. Various oxygen scavengers and dispositions thereof may be suitable, including oxidase enzymes such as glucose oxidase. Small molecule oxygen scavengers may also be suitable, but they may be fully consumed before the sensor lifetime is otherwise fully exhausted. Enzymes, in contrast, may undergo reversible oxidation and reduction, thereby affording a longer sensor lifetime. By discouraging oxidation of the reduced form of sarcosine oxidase with oxygen, the slower electron exchange reaction with the electron transfer agent may occur, thereby allowing production of a current at the working electrode. The magnitude of the current produced is proportional to the amount of creatinine that was initially reacted.

The oxygen scavenger used for encouraging the desired reaction may be an oxidase enzyme in any embodiment of the present disclosure. Any oxidase enzyme may be used to promote oxygen scavenging in proximity to the enzyme system, provided that a suitable substrate for the enzyme is also present, thereby providing a reagent for reacting with the oxygen in the presence of the oxidase enzyme. Oxidase enzymes that may be suitable for oxygen scavenging in the present disclosure include, but are not limited to, glucose oxidase, lactate oxidase, xanthine oxidase, and the like. Glucose oxidase may be a particularly desirable oxidase enzyme to promote oxygen scavenging due to the ready availability of glucose in various bodily fluids. Reaction 1 below shows the enzymatic reaction promoted by glucose oxidase to afford oxygen clearing.

Reaction 1

$$\beta\text{-D-glucose} + O_2 \dashrightarrow \text{D-glucono-1,5-lactone} + H_2O_2$$

The concentration of available lactate in vivo is lower than that of glucose, but still sufficient to promote oxygen scavenging.

Oxidase enzymes, such as glucose oxidase, may be positioned in any location suitable to promote oxygen scavenging in the analyte sensors disclosed herein. Glucose oxidase, for example, may be positioned upon the sensor tail such that the glucose oxidase is functional and/or non-functional for promoting glucose detection. When non-functional for promoting glucose detection, the glucose oxidase may be positioned upon the sensor tail such that electrons produced during glucose oxidation are precluded from reaching the working electrode, such as through electrically isolating the glucose oxidase from the working electrode.

Additional details concerning enzyme systems responsive to creatinine may be found in commonly owned U.S. patent application Ser. No. 16/582,583 entitled "Analyte Sensors and Sensing Methods for Detecting Creatinine," filed on Sep. 25, 2019, and published as U.S. Patent Application Publication 2020/0241015, incorporated herein in its entirety by reference.

In some embodiments, the analyte sensors may comprise a lactate-responsive active area comprising a lactate-responsive enzyme disposed upon the sensor tail. Suitable lactate-responsive enzymes may include, for example, lactate oxidase. Lactate oxidase or other lactate-responsive enzymes may be covalently bonded to a polymer comprising the lactate-responsive active area and exchange electrons with an electron transfer agent (e.g., an osmium (Os) complex or similar transition metal complex), which may also be covalently bonded to the polymer. Suitable electron transfer agents are described in further detail below. An albumin, such as human serum albumin, may be present in the lactate-responsive active area to stabilize the sensor response, as described in further detail in commonly owned U.S. Patent Application Publication 2019/0320947, which is incorporated herein by reference in its entirety. Lactate levels may vary in response to numerous environmental or physiological factors including, for example, eating, stress, exercise, sepsis or septic shock, infection, hypoxia, presence of cancerous tissue, or the like.

In some embodiments, the analyte sensors may comprise an active area responsive to pH. Suitable analyte sensors configured for determining pH are described in commonly owned U.S. Patent Application Publication 2020/0060592, which is incorporated herein by reference in its entirety. Such analyte sensors may comprise a sensor tail comprising a first working electrode and a second working electrode, wherein a first active area located upon the first working electrode comprises a substance having pH-dependent oxidation-reduction chemistry, and a second active area located upon the second working electrode comprises a substance having oxidation-reduction chemistry that is substantially invariant with pH. By obtaining a difference between the first signal and the second signal, the difference may be correlated to the pH of a fluid to which the analyte sensor is exposed.

Two different types of active areas may be located upon a single working electrode, such as the carbon working electrodes discussed above, and spaced apart from one another. Each active area may have an oxidation-reduction potential, wherein the oxidation-reduction potential of the first active area is sufficiently separated from the oxidation-reduction potential of the second active area to allow independent production of a signal from one of the active areas. By way of non-limiting example, the oxidation-reduction potentials may differ by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction may take place within one of the two active areas (i.e., within the first active area or the second active area) without substantially inducing an electrochemical reaction within the other active area. Thus, a signal from one of the first active area or the second active area may be independently produced at or above its corresponding oxidation-reduction potential (the lower oxidation-reduction potential) but below the oxidation-reduction potential of the other active area. A difference signal may allow the signal contribution from each analyte to be resolved.

Some or all embodiments of analyte sensors disclosed herein may feature one or more active areas located upon the surface of at least one working electrode, where the active areas detect the same or different analytes. A membrane may overcoat at least the active area (comprising an analyte-responsive enzyme), and may further overcoat all or a portion of the working electrode lacking an active area (the exposed or extraneous portion of the working electrode). The membrane may be a mass transport limiting membrane and may be a single layer of membrane, a bilayer of two different membrane polymers, or an admixture of two different membrane polymers.

An electron transfer agent may be present in any of the active areas disclosed herein. Suitable electron transfer agents may facilitate conveyance of electrons to the adjacent working electrode after one or more analytes undergoes an enzymatic oxidation-reduction reaction within the corresponding active area, thereby generating an electron flow that is indicative of the presence of a particular analyte. The amount of current generated is proportional to the quantity of analyte that is present. Depending on the sensor configuration used, the electron transfer agents in active areas responsive to different analytes may be the same or different. For example, when two different active areas are disposed upon the same working electrode, the electron transfer agent within each active area may be different (e.g., chemically different such that the electron transfer agents exhibit different oxidation-reduction potentials). When multiple working electrodes are present, the electron transfer agent within each active area may be the same or different, since each working electrode may be interrogated separately.

Suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples of suitable electron transfer agents include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

Active areas suitable for detecting any of the analytes disclosed herein may comprise a polymer to which the electron transfer agents are covalently bound. Any of the electron transfer agents disclosed herein may comprise suitable functionality to promote covalent bonding to the polymer within the active areas. Suitable examples of polymer-bound electron transfer agents may include those described in U.S. Pat. Nos. 8,444,834, 8,268,143 and 6,605,201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(l-vinylimidazole)), or any copolymer thereof. Illustrative copolymers that may be suitable for inclusion in the active areas include those containing monomer units such as styrene, acrylamide, methacrylamide, or acrylonitrile, for example. When two or more different active areas are present, the polymer within each active area may be the same or different.

Covalent bonding of the electron transfer agent to a polymer within an active area may take place by polymerizing a monomer unit bearing a covalently bonded electron transfer agent, or the electron transfer agent may be reacted with the polymer separately after the polymer has already been synthesized. A bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, one or more of the enzymes within the active areas may be covalently bonded to a polymer comprising an active area. When an enzyme system comprising multiple enzymes is present in a given active area, all of the multiple enzymes may be covalently bonded to the polymer in some embodiments, and in other embodiments, only a portion of the multiple enzymes may be covalently bonded to the polymer. For example, one or more enzymes comprising an enzyme system may be covalently bonded to the polymer and at least one enzyme may be non-covalently associated with the polymer, such that the non-covalently bonded enzyme is physically entrained within the polymer. Covalent bonding of the enzyme(s) to the polymer in a given active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidyl ether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments. In particular embodiments, all of the enzymes within a given active area may be covalently bonded to a polymer.

The electron transfer agent and/or the enzyme(s) may be associated with the polymer in an active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained within the polymer without being bonded thereto. Physically entrained electron transfer agents and/or enzyme(s) may still suitably interact with a fluid to promote analyte detection without being substantially leached from the active areas.

The polymer within the active area may be chosen such that outward diffusion of $NAD^+$ or another cofactor not covalently bound to the polymer is limited. Limited outward diffusion of the cofactor may promote a reasonable sensor lifetime (days to weeks) while still allowing sufficient inward analyte diffusion to promote detection.

In some embodiments, a stabilizer may be incorporated into the active area of the analyte sensors described herein to improve the functionality of the sensors and achieve desired sensitivity and stability. Such stabilizers may include an antioxidant and/or companion protein to stabilize the enzyme, for instance. Examples of suitable stabilizers may include, but are not limited to serum albumin (e.g., humane or bovine serum albumin or other compatible albumin), catalase, other enzyme antioxidants, and the like, and any combination thereof. The stabilizers may be conjugated or non-conjugated.

In particular embodiments of the present disclosure, the mass transport limiting membrane overcoating one or more active areas may comprise a crosslinked polyvinylpyridine homopolymer or copolymer. The composition of the mass transport limiting membrane may be the same or different where the mass transport limiting membrane overcoats active areas of differing types. When the membrane composition varies at two different locations, the membrane may comprise a bilayer membrane or a homogeneous admixture of two different membrane polymers, one of which may be a crosslinked polyvinylpyridine or polyvinylimidazole homopolymer or copolymer. Suitable techniques for depositing a mass transport limiting membrane upon the active area may include, for example, spray coating, painting, inkjet printing, screen printing, stenciling, roller coating, dip coating, the like, and any combination thereof. Dip coating techniques may be especially desirable for polyvinylpyridine and polyvinylimidazole polymers and copolymers.

In certain embodiments, the mass transport limiting membrane discussed above is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

In some embodiments, a membrane may be formed by crosslinking in situ a polymer, including those discussed above, modified with a zwitterionic moiety, a non-pyridine copolymer component, and optionally another moiety that is either hydrophilic or hydrophobic, and/or has other desirable properties, in a buffer solution (e.g., an alcohol-buffer solution). The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to “fine-tune” the permeability of the resulting membrane to an analyte of interest. Optional hydrophilic modifiers, such as poly(ethylene glycol), hydroxyl or polyhydroxyl modifiers, and the like, and any combinations thereof, may be used to enhance the biocompatibility of the polymer or the resulting membrane.

In some embodiments, the membrane may comprise a compound including, but not limited to, poly(styrene-co-maleic anhydride), dodecylamine and poly(propylene glycol)-block-poly(ethylene glycol)-block-poly(propylene glycol) (2-aminopropyl ether) crosslinked with poly(propylene glycol)-block-poly(ethylene glycol)-block-poly(propylene glycol) bis(2-aminopropyl ether); poly(N-isopropyl acrylamide); a copolymer of poly(ethylene oxide) and poly (propylene oxide); polyvinylpyridine; a derivative of polyvinylpyridine; polyvinylimidazole; a derivative of polyvinylimidazole; and the like; and any combination thereof. In some embodiments, the membrane may be comprised of a polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group. Other membrane compounds, alone or in combination with any aforementioned membrane compounds, may comprise a suitable copolymer of 4-vinylpyridine and styrene and an amine-free polyether arm.

The membrane compounds described herein may further be crosslinked with one or more crosslinking agents, including those listed above with reference to the enzyme described herein. For example, suitable crosslinking agents may include, but are not limited to, polyethylene glycol diglycidylether (PEGDGE), glycerol triglycidyl ether (Gly3), polydimethylsiloxane diglycidylether (PDMS-DGE), or other polyepoxides, cyanuric chloride, N-hydroxysuccinimide, imidoesters, epichlorohydrin, or derivatized variants thereof, and any combination thereof. Branched versions with similar terminal chemistry are also suitable for the present disclosure. For example, in some embodiments, Formula 1 may be crosslinking with triglycidyl glycerol ether and/or PEDGE and/or polydimethylsiloxane diglycidylether (PDMS-DGE).

A membrane may be formed in situ by applying an alcohol-buffer solution of a crosslinker and a modified polymer over the active area and any additional compounds included in the active area (e.g., electron transfer agent) and allowing the solution to cure for about one to two days or other appropriate time period. The crosslinker-polymer solution may be applied over the active area by placing a droplet or droplets of the membrane solution on at least the sensor element(s) of the sensor tail, by dipping the sensor tail into the membrane solution, by spraying the membrane solution on the sensor, by heat pressing or melting the membrane in any sized layer (such as discrete or all encompassing) and either before or after singulation, vapor deposition of the membrane, powder coating of the membrane, and the like, and any combination thereof. In order to coat the distal and side edges of the sensor, the membrane material may be applied subsequent to application (e.g., singulation) of the sensor electronic precursors (e.g., electrodes). In some embodiments, the analyte sensor is dip-coated following electronic precursor application to apply one or more membranes. Alternatively, the analyte sensor could be slot-die coated wherein each side of the analyte sensor is coated separately. A membrane applied in the above manner may have any of various functions including, but not limited to, mass transport limitation (i.e., reduction or elimination of the flux of one or more analytes and/or compounds that reach the active area), biocompatibility enhancement, interferent reduction, and the like, and any combination thereof.

Generally, the thickness of the membrane is controlled by the concentration of the membrane solution, by the number of droplets of the membrane solution applied, by the number of times the sensor is dipped in the membrane solution, by the volume of membrane solution sprayed on the sensor, and the like, and by any combination of these factors. In some embodiments, the membrane described herein may have a thickness ranging from about 0.1 micrometers (μm) to about 1000 μm, encompassing any value and subset therebetween and in which the upper and lower limits are separable. As stated above, the membrane may overlay one or more active areas, and in some embodiments, the active areas may have a thickness of from about 0.1 μm to about 50 μm, encompassing any value and subset therebetween and in which the upper and lower limits are separable. In some embodiments, a series of droplets may be applied atop one another to achieve the desired thickness of the active area and/or membrane, without substantially increasing the diameter of the applied droplets (i.e., maintaining the desired diameter or range thereof). Each single droplet for example may be applied and then allowed to cool or dry, followed by one or more additional droplets. Active areas and membrane may, but need not be, the same thickness throughout or composition throughout.

In some embodiments, the membrane composition for use as a mass transport limiting layer of the present disclosure may comprise polydimethylsiloxane (PDMS), polydimethylsiloxane diglycidylether (PDMS-DGE), aminopropyl terminated polydimethylsiloxane, and the like, and any combination thereof for use as a leveling agent (e.g., for reducing the contact angel of the membrane composition or active area composition). Branched versions with similar terminal chemistry are also suitable for the present disclosure. Certain leveling agents may additionally be included, such as those found, for example, in U.S. Pat. No. 8,983,568, the disclosure of which is incorporated by reference herein in its entirety.

In some instances, the membrane may form one or more bonds with the active area. As used herein, the term "bonds," and grammatical variants thereof, refers to any type of an interaction between atoms or molecules that allows chemical compounds to form associations with each other, such as, but not limited to, covalent bonds, ionic bonds, dipole-dipole interactions, hydrogen bonds, London dispersion forces, and the like, and any combination thereof. For example, in situ polymerization of the membrane can form crosslinks between the polymers of the membrane and the polymers in the active area. In some embodiments, crosslinking of the membrane to the active area facilitates a reduction in the occurrence of delamination of the membrane from the sensor.

Embodiments disclosed herein include:

A. A method comprising: laser singulating a working electrode comprising an active area disposed thereon, the active area having an analyte-responsive enzyme, wherein the resultant laser singulated working electrode comprises electrode asperities; and laser planing at least a portion of the electrode asperities, the laser planing being recessed from an edge of the laser singulated working electrode, and thereby resulting in a laser planed working electrode.

B. An analyte sensor comprising: a working electrode comprising an active area disposed thereon, the active area having an analyte-responsive enzyme, wherein the working electrode is first laser singulated, thereby resulting in electrode asperities, and thereafter an edge of the working electrode is laser planed to remove at least a portion of electrode asperities therefrom, thereby resulting in a laser planed working electrode.

C. A method comprising: laser singulating a working electrode comprising an active area disposed thereon, the active area having an analyte-responsive enzyme, wherein the resultant laser singulated working electrode comprises electrode asperities; disposing a membrane upon at least a portion of the active area; and laser planing at least a portion of the electrode asperities, the laser planing being recessed from an edge of the laser singulated working electrode, and thereby resulting in a laser planed working electrode.

D. An analyte sensor comprising: a laser planed working electrode comprising an active area disposed thereon and electrode asperities laser planed therefrom, the active area comprising an analyte-responsive enzyme.

E. A method comprising: exposing an analyte sensor to a bodily fluid, the analyte sensor comprising a laser planed working electrode comprising an active area disposed thereon and electrode asperities laser planed therefrom, the active area comprising an analyte-responsive enzyme.

Embodiment A may have one or more of the following additional elements in any combination:

Element A1: wherein the laser planed working electrode exhibits a reduction in interferent signal of an interferent compared to a working electrode that has not been planed.

Element A2: wherein the laser planed working electrode exhibits a reduction in interferent signal of an interferent compared to a working electrode that has not been planed, the reduction in interferent signal of the interferent being greater than about 20%.

Element A3: wherein the laser planed working electrode exhibits a reduction in interferent signal of an interferent compared to a working electrode that has not been planed, the reduction in interferent signal of the interferent being in the range about 20% to about 70%, encompassing any value and subset therebetween and in which the upper and lower limits are separable.

Element A4: wherein the laser planed working electrode exhibits a reduction in interferent signal of an interferent compared to a working electrode that has not been planed, the interferent being ascorbic acid.

Element A5: further comprising removing at least about 5% of a total area of the electrode asperities.

Element A6: further comprising removing in the range of about 5% to about 75% of a total area of the electrode asperities, encompassing any value and subset therebetween and in which the upper and lower limits are separable.

Element A7: wherein the laser planing comprises a plurality of single-pass laser planing cuts.

Element A8: wherein the laser planing comprises a plurality of single-pass laser planing cuts, the plurality of single-pass laser planing cuts being at least one of perpendicular to the edge of the laser singulated working electrode or beveled relative to the edge of the laser singulated working electrode.

Element A9: wherein the electrode asperities have a width in the range of 1 μm to about 75 encompassing any value and subset therebetween and in which the upper and lower limits are separable.

Element A10: wherein the electrode asperities have a height of about 1 μm to about encompassing any value and subset therebetween and in which the upper and lower limits are separable.

Element A11: wherein the active area is comprised of a plurality of discontiguous active areas or a single contiguous active area.

Element A12: wherein the active area is compressed.

Element A13: wherein the active-responsive enzyme is a glucose-responsive enzyme.

Element A14: wherein a membrane is disposed upon at least a portion of the active area.

By way of non-limiting example, exemplary combinations applicable to A include, but are not limited to: A with any one or more or all of A1-A14, in any combination.

Embodiment B may have one or more of the following additional elements in any combination:

Element B1: wherein the laser planed working electrode exhibits a reduction in interferent signal of an interferent compared to a working electrode that has not been planed.

Element B2: wherein the laser planed working electrode exhibits a reduction in interferent signal of an interferent compared to a working electrode that has not been planed, the reduction in interferent signal of the interferent being greater than about 20%.

Element B3: wherein the laser planed working electrode exhibits a reduction in interferent signal of an interferent compared to a working electrode that has not been planed, the reduction in interferent signal of the interferent being in the range about 20% to about 70%, encompassing any value and subset therebetween and in which the upper and lower limits are separable.

Element B4: wherein the laser planed working electrode exhibits a reduction in interferent signal of an interferent compared to a working electrode that has not been planed, the interferent being ascorbic acid.

Element B5: wherein at least about 5% of a total area of the electrode asperities is removed.

Element B6: wherein in the range of about 5% to about 75% of a total area of the electrode asperities is removed, encompassing any value and subset therebetween and in which the upper and lower limits are separable.

Element B7: wherein the electrode asperities have a width in the range of 1 μm to about 75 μm, encompassing any value and subset therebetween and in which the upper and lower limits are separable.

Element B8: wherein the electrode asperities have a height of about 1 μm to about 50 μm, encompassing any value and subset therebetween and in which the upper and lower limits are separable.

Element B9: wherein the active area is comprised of a plurality of discontiguous active areas or a single contiguous active area.

Element B10: wherein the active area is compressed.

Element B11: wherein the active-responsive enzyme is a glucose-responsive enzyme.

Element B12: wherein a membrane is disposed upon at least a portion of the active area.

By way of non-limiting example, exemplary combinations applicable to B include, but are not limited to: B with any one or more or all of B1-B12, in any combination.

Embodiment C may have one or more of the following additional elements in any combination:

Element C1: wherein the laser planed working electrode exhibits a reduction in interferent signal of an interferent compared to a working electrode that has not been planed.

Element C2: wherein the laser planed working electrode exhibits a reduction in interferent signal of an interferent compared to a working electrode that has not been planed, the reduction in interferent signal of the interferent being greater than about 20%.

Element C3: wherein the laser planed working electrode exhibits a reduction in interferent signal of an interferent compared to a working electrode that has not been planed, the reduction in interferent signal of the interferent being in the range about 20% to about 70%, encompassing any value and subset therebetween and in which the upper and lower limits are separable.

Element C4: wherein the laser planed working electrode exhibits a reduction in interferent signal of an interferent compared to a working electrode that has not been planed, the interferent being ascorbic acid.

Element C5: further comprising removing at least about 5% of a total area of the electrode asperities.

Element C6: further comprising removing in the range of about 5% to about 75% of a total area of the electrode asperities, encompassing any value and subset therebetween and in which the upper and lower limits are separable.

Element C7: wherein the laser planing comprises a plurality of single-pass laser planing cuts.

Element C8: wherein the laser planing comprises a plurality of single-pass laser planing cuts, the plurality of single-pass laser planing cuts being at least one of perpendicular to the edge of the laser singulated working electrode or beveled relative to the edge of the laser singulated working electrode.

Element C9: wherein the electrode asperities have a width in the range of 1 μm to about 75 μm, encompassing any value and subset therebetween and in which the upper and lower limits are separable.

Element C10: wherein the electrode asperities have a height of about 1 μm to about 50 μm, encompassing any value and subset therebetween and in which the upper and lower limits are separable.

Element C11: wherein the active area is comprised of a plurality of discontiguous active areas or a single contiguous active area.

Element C12: wherein the active area is compressed.

Element C13: wherein the active-responsive enzyme is a glucose-responsive enzyme.

By way of non-limiting example, exemplary combinations applicable to C include, but are not limited to: C with any one or more or all of C1-C13, in any combination.

Embodiments D and E may have one or more of the following additional elements in any combination:

Element D/E1: wherein the laser planed working electrode exhibits a reduction in interferent signal of an interferent compared to a working electrode that has not been planed.

Element D/E2: wherein the laser planed working electrode exhibits a reduction in interferent signal of an interferent compared to a working electrode that has not been planed, the reduction in interferent signal of the interferent being greater than about 20%.

Element D/E3: wherein the laser planed working electrode exhibits a reduction in interferent signal of an interferent compared to a working electrode that has not been planed, the reduction in interferent signal of the interferent being in the range about 20% to about 70%, encompassing any value and subset therebetween and in which the upper and lower limits are separable.

Element D/E4: wherein the laser planed working electrode exhibits a reduction in interferent signal of an interferent compared to a working electrode that has not been planed, the interferent being ascorbic acid.

Element D/E5: wherein at least about 5% of a total area of the electrode asperities is removed.

Element D/E6: wherein in the range of about 5% to about 75% of a total area of the electrode asperities is removed, encompassing any value and subset therebetween and in which the upper and lower limits are separable.

Element D/E7: wherein the electrode asperities have a width in the range of 1 μm to about 75 μm, encompassing any value and subset therebetween and in which the upper and lower limits are separable.

Element D/E8: wherein the electrode asperities have a height of about 1 μm to about 50 μm, encompassing any value and subset therebetween and in which the upper and lower limits are separable.

Element D/E9: wherein the active area is comprised of a plurality of discontiguous active areas or a single contiguous active area.

Element D/E10: wherein the active area is compressed.

Element D/E11: wherein the active-responsive enzyme is a glucose-responsive enzyme.

Element D/E12: wherein a membrane is disposed upon at least a portion of the active area.

By way of non-limiting example, exemplary combinations applicable to D/E include, but are not limited to: D/E with any one or more or all of D/E1-D/E12, in any combination.

To facilitate a better understanding of the embodiments described herein, the following examples of various representative embodiments are given. In no way should the following examples be read to limit, or to define, the scope of the invention.

Figure 9A:
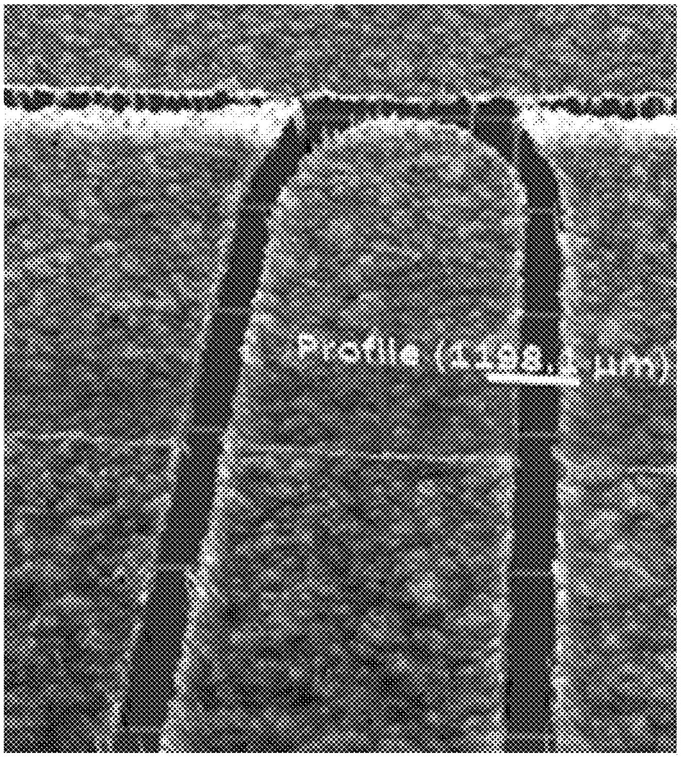
FIG. 9A shows a photograph of a top view of a working electrode having no membrane and no active area disposed thereon.
Figure 9B:
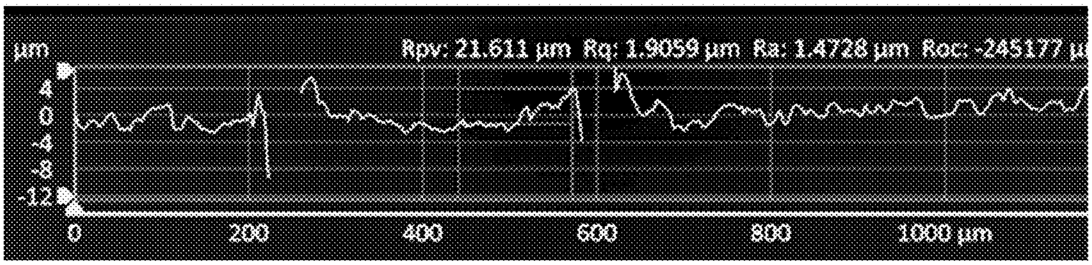
FIG. 9B is a depth profile along the line indicated in FIG. 9A.

Example 1. In this Example, laser planing was performed on the example laser singulated working electrode shown in FIG. 9A. FIG. 9A does not comprise an active area disposed thereupon. FIG. 9B shows a 3D optical profile of a portion of the singulated working electrode of FIG. 9A, evaluated along the identified profile width. The 3D optical profile was obtained using a ZEGAGE™ 3D Optical Profiler, ZYGOO® Corporation (Middlefield, CT). As shown in FIG. 9B, the electrode asperities at the edge of the singulated sensor tail exhibited a height of about 1 μm to about 5 μm.

Figure 9C:
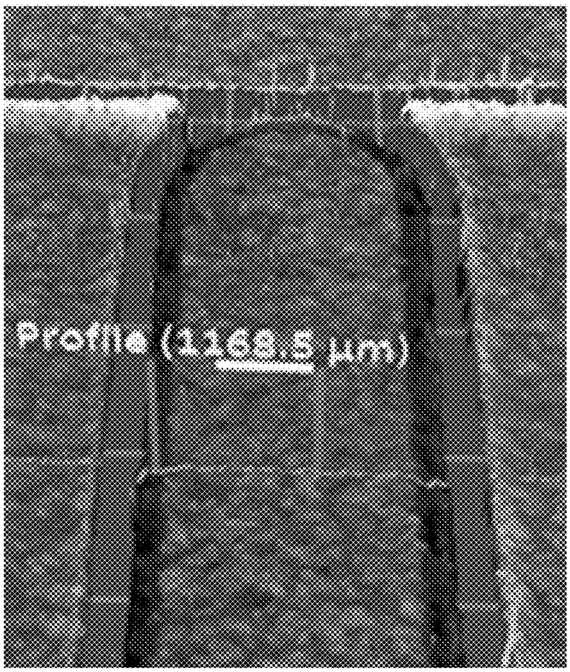
FIG. 9C shows a photograph of a top view of the working electrode of FIG. 9A after laser planing, in accordance with one or more aspects of the present disclosure.
Figure 9D:
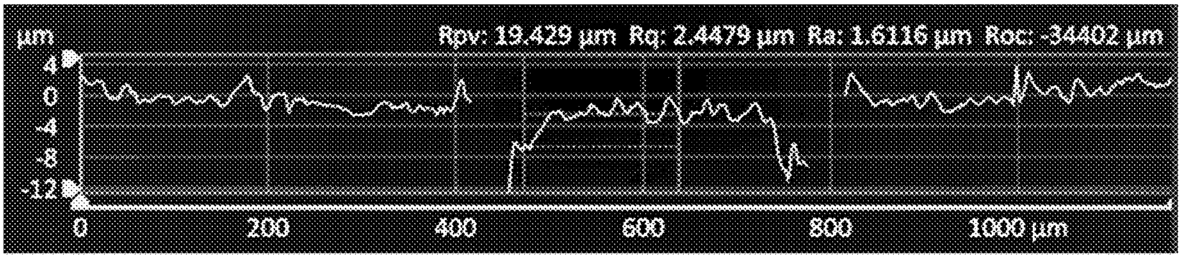
FIG. 9D is a depth profile along the line indicated in FIG. 9C.

Laser planing was performed using three single-pass laser lines positioned at the edge of the carbon asperities and made about 5 μm to about 20 μm, such as about 5 μm to about 10 μm, apart progressively toward the midline of the electrode at 10% laser power. In the examples described herein, a UV laser was used, but it is to be appreciated that any laser may be used to perform laser planing, without departing from the scope of the present disclosure. FIG. 9C is a photograph of the planed sensor tail, showing the beveled edge of the working electrode of the sensor tail. FIG. 9D is a 3D optical profile (obtained as previously described) along the identified profile line showing the electrode asperities removed.

Figure 10A:
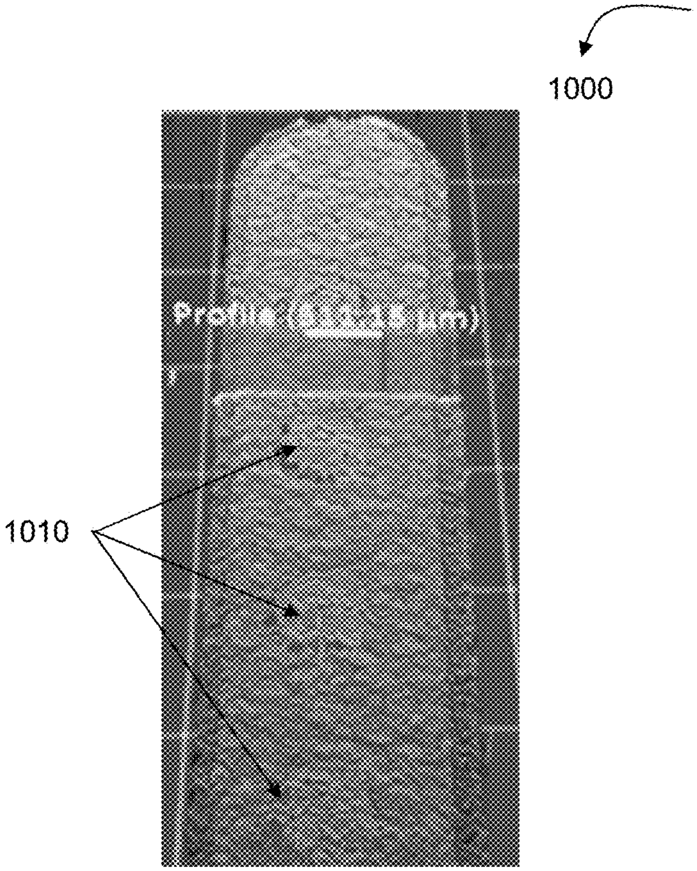
FIG. 10A shows a photograph of a top view of a working electrode having no membrane and an active area disposed thereon after laser planing, in accordance with one or more aspects of the present disclosure.
Figure 10B:
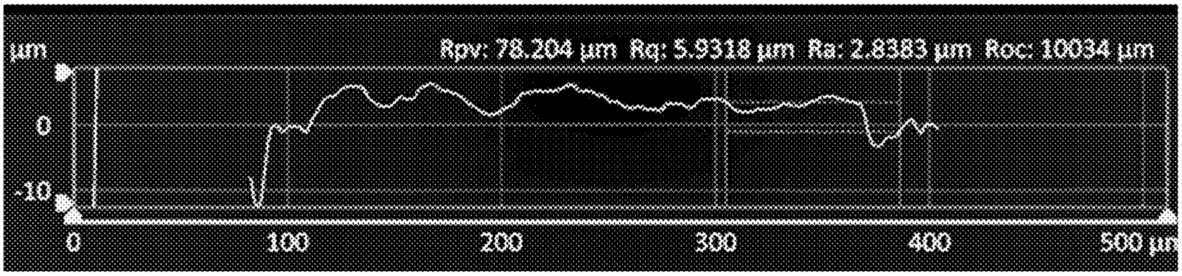
FIG. 10B is a depth profile along the line indicated in FIG. 10A.

Example 2. In this Example, and with reference to FIG. 10A, a laser planed carbon working electrode 1000 was prepared in accordance with Example 1, the carbon electrode comprising active areas 1010 dispensed thereupon. The unplaned carbon electrode comprising active areas 1010 is not shown, but will be referred to as "unplaned, dispensed" electrode. FIG. 10B is a 3D optical profile (obtained as previously described) along the identified profile line showing minimal electrode asperities as a result of the planing.

Figure 11:
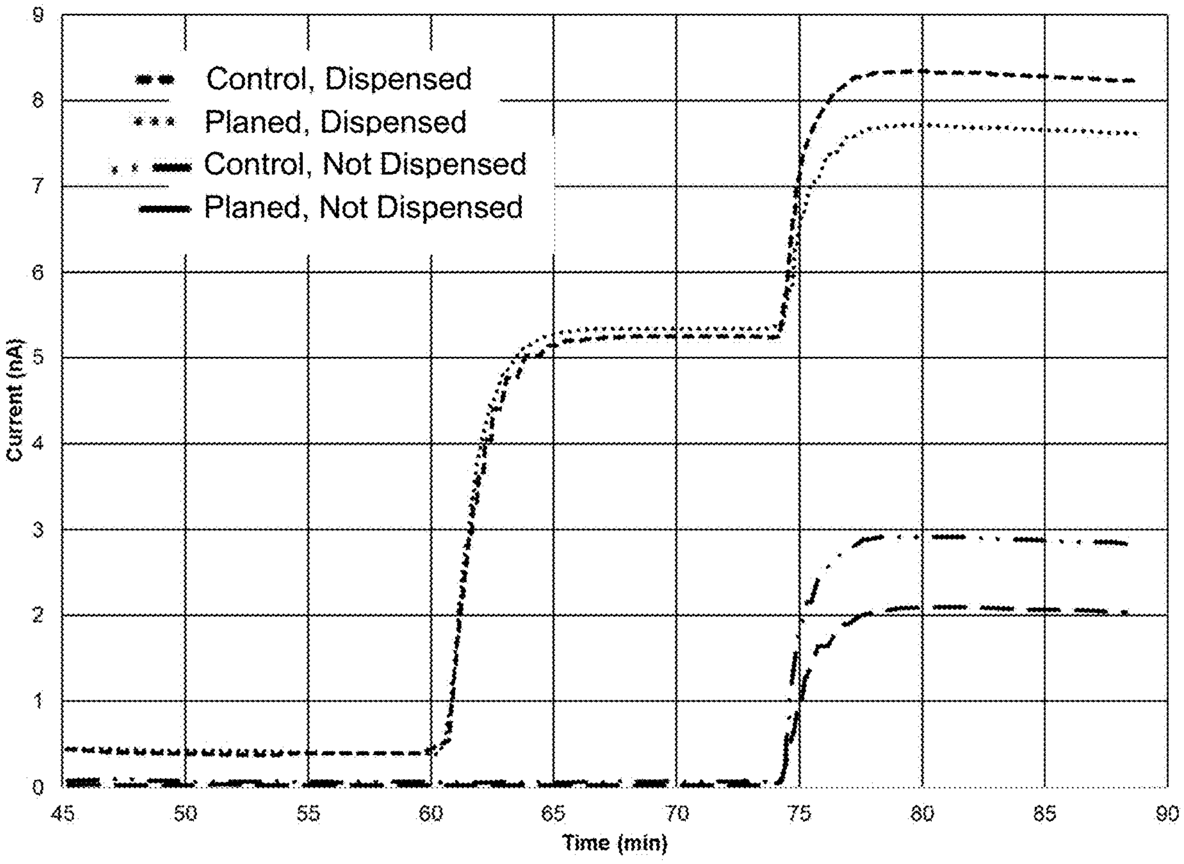
FIG. 11 is a graph of a paired-difference test comparing planed and unplaned working electrodes having either an active area or lacking an active area in response to the interferent ascorbic acid.

Example 3. A paired-difference test was performed. The unplaned electrode of FIG. 9A and planed electrode of FIG. 9C having no active area ("not planed, not dispensed" and "planed, not dispensed," respectively) were examined with the "unplaned, dispensed" electrode of Example 2 and the planed electrode of FIG. 10A having multiple sensing spots ("planed, dispensed") were evaluated in 100 mM PBS at 37° C. separately in 50 mg/dL glucose and 2 mg/dL ascorbic acid. The results are provided in Table 1 below, and graphically represented in FIG. 11.

TABLE 1

| | Iavg (nA) n = 8* | | | |
|---|---|---|---|---|
| | Undispensed | | Dispensed | |
| | Not Planed (FIG. 9A) | Planed (FIG. 9C) | Not Planed | Planed (FIG. 10A) |
| Glucose | ~0 | ~0 | ~5 | ~5 |
| Ascorbic Acid | ~3 | ~2 | ~3 | ~2 |
| % Δ** | ~-30 | | ~-25 | |

*background corrected;
**laser-planed relative to control

As shown, the paired-different test demonstrates that the laser planed electrodes demonstrate a reduction in 2 mg/dL of ascorbic acid by about 25% to about 30% compared to the unplaned counterparts.

Example 4. Paired-difference tests were performed on the following prepared laser singulated working electrodes. The unplaned "control" working electrodes comprised active areas of multiple sensing spots. The electrodes described as "compressed" comprise the same concentration of active area (compressed active area), but the multiple sensing spots are closer together and/or closer to the tip of the electrode. For example, the pitch between each discontiguous active area (the distance between adjacent sensing spots) may be about 50 μm to about 800 μm, such as about 50 μm to about 500 μm, encompassing any value and subset therebetween and in which the upper and lower limits are separable. As used herein, the term "pitch," and grammatical variants thereof, refers to the spacing between adjacent sensing spots in an active area sensing layer, measured from the center of each adjacent sensing spot. Typically, the distal most active area is located at least about 200 μm to 300 μm (measured from the center of the sensing thereof) from the tip of the working electrode (which may be identical to the tip of the sensor tail) to be located most distally into bodily fluid, but may be in the range of about 50 μm to about 500 μm, encompassing any value and subset therebetween and in which the upper and lower limits are separable.

The totality of analyte-responsive enzyme for all samples was the same, whether compressed or not. Laser planing is described with reference to three separate single-pass laser lines, each a particular distance from the edge of the initial unplaned electrode (the "planing scheme"). For example, "20-40-60" refers to a first single-pass laser line at 20 μm from the edge of the unplaned electrode, a second single-pass laser line at 40 μm from the edge of the unplaned electrode, and a third single-pass laser line at 60 μm from the edge of the unplaned electrode.

TABLE 2

Figures 12A, 12B, 12C, 12D, 12E:
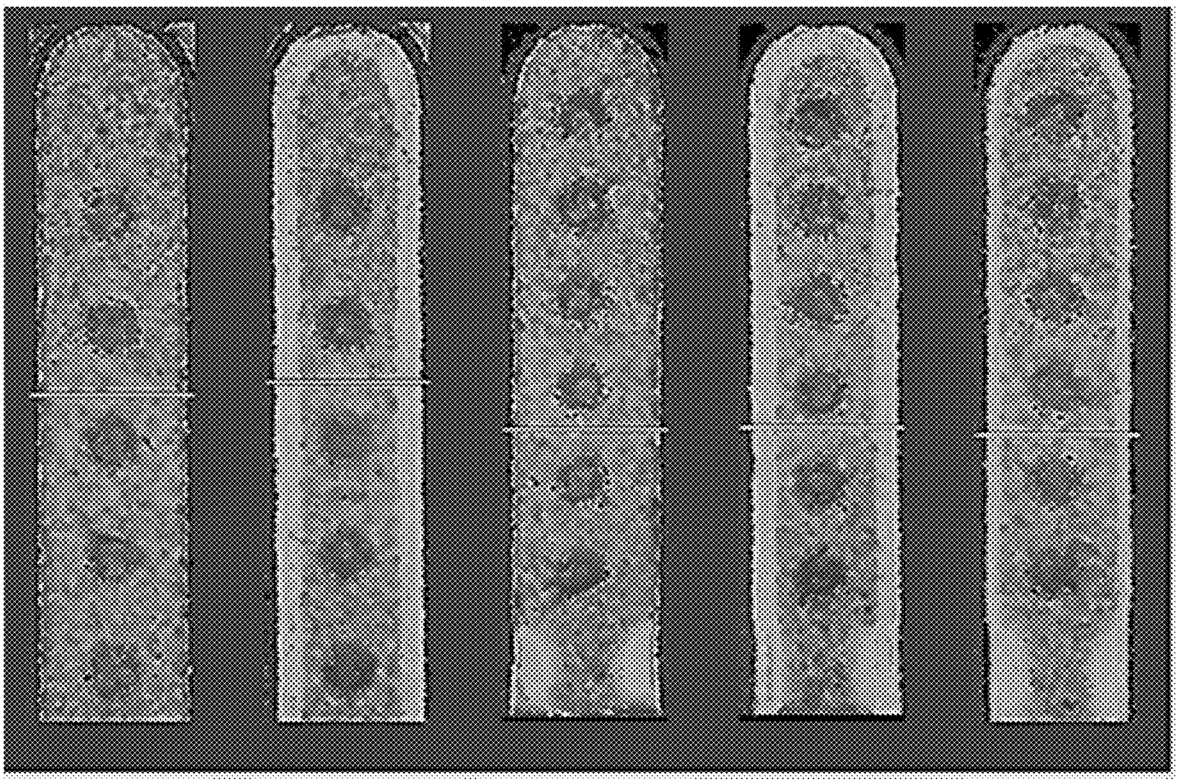
FIGS. 12A-12E show photographs of working electrodes.

| | FIG. 12A | FIG. 12B | FIG. 12C | FIG. 12D | FIG. 12E |
|---|---|---|---|---|---|
| Compressed? | No | No | Yes | Yes | Yes |
| Planing Scheme | Unplaned | 20-40-60 | Unplaned | 20-40-60 | 15-25-40 |

The electrodes 12A-12E described in Table 2 in some instances were coated with a mass transport limiting membrane having the thickness shown in Table 3 below. Paired-difference tests (avg. of n=6/condition) were performed in 100 mM PBS at 37° C. separately in 50 mg/dL glucose and 2 mg/dL ascorbic acid. The results are provided in Table 3 below.

TABLE 3

| | Planing? | Membrane Thickness | % Δ |
|---|---|---|---|
| 12A | No | ~35 μm | ~0 |
| 12A | No | ~50 μm | ~−20 |
| 12B | 20-40-60 | ~35 μm | ~−30 |
| 12B | 20-40-60 | ~50 μm | ~−45 |
| 12C | No | ~35 μm | ~−50 |
| 12C | No | ~50 μm | ~−50 |
| 12D | 20-40-60 | ~35 μm | ~−50 |
| 12D | 20-40-60 | ~50 μm | ~−65 |
| 12E | 15-25-40 | ~35 μm | ~−50 |
| 12E | 15-25-40 | ~50 μm | ~−60 |

As shown in Table 3, the paired-different test in this example demonstrates that the laser planed electrodes may demonstrate a reduction in ascorbic acid signal interference by greater than about 20% compared to the unplaned counterparts. Accordingly, the embodiments of the present disclosure permit at least a reduction in interferent signal, such as ascorbic acid, in the range of greater than about 20%, which may be up to 100% depending on the configuration of the analyte sensor, or such as in the range of about 20% to about 70% or greater, and preferably at least about 40% greater, at least about 45% greater, or at least about 50%, encompassing any value and subset therebetween and in which the upper and lower limits are separable. Further, the results indicate that even a relatively small laser planing amount can be effective.

Accordingly, the present disclosure provides analyte sensors for monitoring various analytes in vivo. The analyte sensors may feature enhancements to address signals obtained from interferent species. Some analyte sensors may comprise an analyte sensor comprising a working electrode comprising an active area disposed thereon and electrode asperities laser planed therefrom, the active area comprising an analyte-responsive enzyme. Methods include laser singulating a working electrode, the working electrode comprising an active area disposed thereupon and electrode asperities, the active area comprising an analyte-responsive enzyme, and laser planing at least a portion of the electrode asperities.

Unless otherwise indicated, all numbers expressing quantities and the like in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A method of creating a laser planed working electrode comprising:

laser singulating a working electrode from a template carbon substrate material into a shape, the working electrode comprising an active area disposed thereon, the active area having an analyte-responsive enzyme, wherein the laser singulated working electrode comprises electrode asperities at an outermost edge thereof; and laser planing at least a portion of the outermost edge to remove at least a portion of the electrode asperities at the outermost edge, wherein the laser planing comprises making a plurality of spaced apart cuts between a midline length and the outermost edge of the laser singulated working electrode to create an outer beveled edge of the shape, thereby resulting in the laser planed working electrode, wherein a depth of each of the plurality of spaced apart cuts is less than a thickness of the working electrode.

2. The method of claim 1, wherein the laser planed working electrode exhibits a reduction in interferent signal of an interferent compared to a working electrode that has not been planed.

3. The method of claim 2, wherein the reduction in interferent signal of the interferent is greater than 20%.

4. The method of claim 2, wherein the interferent is ascorbic acid.

5. The method of claim 1, further comprising removing at least 5% of a total area of the electrode asperities.

6. The method of claim 1, wherein the laser planing comprises a plurality of single-pass laser planing cuts.

7. The method of claim 6, wherein the plurality of single-pass laser planing cuts are at least one of perpendicular to the outermost edge of the laser singulated working electrode or beveled relative to the outermost edge of the laser singulated working electrode.

8. The method of claim 1, wherein the electrode asperities have a width in the range of 1 μm to 75 μm and a height of 1 μm to 50 μm.

9. The method of claim 1, wherein the active area is comprised of a plurality of discontiguous active areas.

10. The method of claim 1, wherein the active area is comprised of a single contiguous active area.

11. The method of claim 1, wherein the active area is compressed.

12. The method of claim 1, wherein the analyte-responsive enzyme is a glucose-responsive enzyme.

13. The method of claim 1, wherein a membrane is disposed upon at least a portion of the active area.

14. The method of claim 1, wherein the plurality of spaced apart cuts comprises at least cuts at 20 μm, 40 μm, and 60 μm from the outermost edge of the laser singulated working electrode.

15. An analyte sensor comprising:

a working electrode comprising an active area disposed thereon, the active area having an analyte-responsive enzyme, wherein the working electrode is first laser singulated from a template carbon substrate material, thereby resulting in electrode asperities at an edge thereof, and thereafter the edge of the working electrode is laser planed to remove at least a portion of the electrode asperities therefrom at the edge, thereby resulting in a laser planed working electrode, wherein the laser singulated working electrode is laser planed by making a plurality of spaced apart cuts between a midline length and an outermost edge of the working electrode to create an outer beveled edge, wherein a depth of each of the plurality of spaced apart cuts is less than a thickness of the working electrode.

16. The analyte sensor of claim 15, wherein the laser planed working electrode exhibits a reduction in interferent signal of an interferent compared to a working electrode that has not been planed.

17. The analyte sensor of claim 16, wherein the reduction in interferent signal of the interferent is greater than 20%.

18. The analyte sensor of claim 16, wherein the interferent is ascorbic acid.

19. The analyte sensor of claim 15, wherein at least 5% of a total area of the electrode asperities is removed.

20. The analyte sensor of claim 15, wherein the electrode asperities have a width in the range of 1 μm to 75 μm and have a height of 1 μm to 50 μm.

21. The analyte sensor of claim 15, wherein the active area is comprised of a plurality of discontiguous active areas.

22. The analyte sensor of claim 15, wherein the active area is comprised of a single contiguous active area.

23. The analyte sensor of claim 15, wherein the active area is compressed.

24. The analyte sensor of claim 15, wherein the laser planing comprises at least cuts at 20 μm, 40 μm, and 60 μm from the outermost edge of the working electrode.

* * * * *